(12) United States Patent
Zhang et al.

(10) Patent No.: US 12,195,740 B2
(45) Date of Patent: Jan. 14, 2025

(54) TRANSCRIPTION REGULATING NUCLEOTIDE SEQUENCES AND METHODS OF USE

(71) Applicant: BASF Agricultural Solutions Seed US LLC, Florham Park, NJ (US)

(72) Inventors: Shirong Zhang, Morrisville, NC (US); Marie-Laure Sauer, Morrisville, NC (US); Lei Ding, Morrisville, NC (US); Soundarya Srirangan, Morrisville, NC (US); Timothy Eberle, Cary, NC (US); Joshua Kent Sailsbery, Holly Springs, NC (US)

(73) Assignee: BASF AGRICULTURAL SOLUTIONS SEED US LLC, Florham Park, NJ (US)

( * ) Notice: Subject to any disclaimer, the term of this patent is extended or adjusted under 35 U.S.C. 154(b) by 41 days.

(21) Appl. No.: 17/910,432

(22) PCT Filed: Mar. 11, 2021

(86) PCT No.: PCT/US2021/021967
§ 371 (c)(1),
(2) Date: Sep. 9, 2022

(87) PCT Pub. No.: WO2021/183803
PCT Pub. Date: Sep. 16, 2021

(65) Prior Publication Data
US 2023/0137924 A1     May 4, 2023

Related U.S. Application Data

(60) Provisional application No. 63/116,376, filed on Nov. 20, 2020, provisional application No. 62/988,238, filed on Mar. 11, 2020.

(51) Int. Cl.
*C12N 15/82* (2006.01)

(52) U.S. Cl.
CPC .................. *C12N 15/8271* (2013.01)

(58) Field of Classification Search
None
See application file for complete search history.

(56) References Cited

U.S. PATENT DOCUMENTS 9,447,423 B2 * 9/2016 Elich .................. C12N 15/8286

FOREIGN PATENT DOCUMENTS

| WO | WO-2013/040213 A1 | 3/2013 |
| WO | WO-2014/025860 A1 | 2/2014 |
| WO | WO-2014/150449 A2 | 9/2014 |

OTHER PUBLICATIONS

Zrimec, et al. Nature communications 13.1 (2022): 5099. (Year: 2022).*
SoyBase Sequence Feature Glyma13g33190 (Available: Aug. 5, 2010) https://www.soybase.org/sbt/search/search_results.php?category=FeatureName&version=Glyma1.0&search_term=Glyma13g33190 (Year: 2010).*
International Application No. PCT/US2021/021967, International Search Report and Written Opinion, mailed Jun. 25, 2021.

* cited by examiner

*Primary Examiner* — Bratislav Stankovic
(74) *Attorney, Agent, or Firm* — ArentFox Schiff LLP

(57) ABSTRACT

Described herein are nucleic acid having constitutive promoter activities and the use of such nucleic acid having constitutive promoter activities to express a polynucleotide of interest in plants.

16 Claims, 9 Drawing Sheets
Specification includes a Sequence Listing.

SEQUENCE LISTING

<160> NUMBER OF SEQ ID NOS: 6

<210> SEQ ID NO 1
<211> LENGTH: 1080
<212> TYPE: DNA
<213> ORGANISM: Glycine Max

<400> SEQUENCE: 1
ctccgaatat ctcttagttg gaaaaaaaca tttcatcttt taaaaactag atcaaacttg    60

```
ttgtttccac cacaaattgg tttgctttaa gggataatta tgattttga tctgtggact    120 tttttggatt tttaattta gtctttaaac aaaaaattag ctagttgtaa ttgttaaagt    180
tatcatccgt taacatttt ggtcccttcc attaagtgtt gtcattaaca gatgatgtga    240
cgatagctgt gagtgtcatg tggtacttat ttgtggcaat ttattttgtt acgattttgg    300
ctgtcagaaa atgcttactg agttgctttg aaaggtatta acatttttc tacggtttaa    360 aacctctaga aattgctact catgcataca tcatcaacaa attttgtata aagacgattc    420
tcccacaaag tttcatcttt tttttaata acacaaattc atatagactt aattcactca    480
atcacctatg agtaaagatt gcgtctgaga agaaatttacc acacatttct agctttatca    540
tcatatatat ttttcaaaat ttgaggtgaa cataccatca attcatcatc acactaactt    600
aatggtaaac accatcatct atactttcc aaattacaac atcaggcttt ccatccaaat    660
ggaaagtcat aatagagtta ttgtttgggc atgaaaaatg gttctcaatc ttgtaaggaa    720
aaacttaagt ttaatcccga catagtacac ttttaaatct ggattgatga ttagtcttat    780
aattagtcaa aaagattcta attaaggtgg tataaaaaaa tgatcaacta atgtgatgaa    840
actgaagaaa caatttgagc taattgatat taaaaaaaaa aaactctgta aagttaaagg    900
aataatttga aaccaaaaat aaaaaacaat tgtatttaa cctaatagta tttaaattaa    960
aaataataat atactccgag aagaagggaa tatataagaa gagcggcgga gctaaagaag   1020
agagtgggca tagtagacga gaaaggagaa gaagagaatc ataagaaagc aagaaagaaa   1080

<210> SEQ ID NO 2
<211> LENGTH: 880
<212> TYPE: DNA
<213> ORGANISM: Glycine Max

<400> SEQUENCE: 2
ggtcccttcc attaagtgtt gtcattaaca gatgatgtga cgatagctgt gagtgtcatg     60
tggtacttat ttgtggcaat ttattttgtt acgattttgg ctgtcagaaa atgcttactg    120
agttgctttg aaaggtatta acatttttc tacggtttaa aacctctaga aattgctact    180
catgcataca tcatcaacaa attttgtata aagacgattc tcccacaaag tttcatcttt    240 tttttaata acacaaattc atatagactt aattcactca atcacctatg agtaaagatt    300
gcgtctgaga agaaatttacc acacatttct agctttatca tcatatatat ttttcaaaat    360
ttgaggtgaa cataccatca attcatcatc acactaactt aatggtaaac accatcatct    420 atactttcc aaattacaac atcaggcttt ccatccaaat ggaaagtcat aatagagtta    480
ttgtttgggc atgaaaaatg gttctcaatc ttgtaaggaa aaacttaagt ttaatcccga    540
catagtacac ttttaaatct ggattgatga ttagtcttat aattagtcaa aaagattcta    600
attaaggtgg tataaaaaaa tgatcaacta atgtgatgaa actgaagaaa caatttgagc    660
taattgatat taaaaaaaaa aaactctgta aagttaaagg aataatttga aaccaaaaat    720
aaaaaacaat tgtatttaa cctaatagta tttaaattaa aaataataat atactccgag    780
aagaagggaa tatataagaa gagcggcgga gctaaagaag agagtgggca tagtagacga    840
gaaaggagaa gaagagaatc ataagaaagc aagaaagaaa                          880

<210> SEQ ID NO 3
<211> LENGTH: 680
<212> TYPE: DNA
<213> ORGANISM: Glycine Max

<400> SEQUENCE: 3
```

-continued

| | |
|---|---|
| attttgtata aagacgattc tcccacaaag tttcatcttt tttttaata acacaaattc | 60 |
| atatagactt aattcactca atcacctatg agtaaagatt gcgtctgaga agaatttacc | 120 |
| acacatttct agctttatca tcatatatat ttttcaaaat ttgaggtgaa cataccatca | 180 |
| attcatcatc acactaactt aatggtaaac accatcatct atactttcc aaattacaac | 240 |
| atcaggcttt ccatccaaat ggaaagtcat aatagagtta ttgtttgggc atgaaaaatg | 300 |
| gttctcaatc ttgtaaggaa aaacttaagt ttaatcccga catagtacac ttttaaatct | 360 |
| ggattgatga ttagtcttat aattagtcaa aaagattcta attaaggtgg tataaaaaaa | 420 |
| tgatcaacta atgtgatgaa actgaagaaa caatttgagc taattgatat taaaaaaaaa | 480 |
| aaactctgta aagttaaagg aataatttga aaccaaaaat aaaaaacaat tgtattttaa | 540 |
| cctaatagta tttaaattaa aaataataat atactccgag aagaagggaa tatataagaa | 600 |
| gagcggcgga gctaaagaag agagtgggca tagtagacga gaaggagaa gaagagaatc | 660 |
| ataagaaagc aagaaagaaa | 680 |

<210> SEQ ID NO 4
<211> LENGTH: 480
<212> TYPE: DNA
<213> ORGANISM: Glycine Max

<400> SEQUENCE: 4

| | |
|---|---|
| aatggtaaac accatcatct atactttcc aaattacaac atcaggcttt ccatccaaat | 60 |
| ggaaagtcat aatagagtta ttgtttgggc atgaaaaatg gttctcaatc ttgtaaggaa | 120 |
| aaacttaagt ttaatcccga catagtacac ttttaaatct ggattgatga ttagtcttat | 180 |
| aattagtcaa aaagattcta attaaggtgg tataaaaaaa tgatcaacta atgtgatgaa | 240 |
| actgaagaaa caatttgagc taattgatat taaaaaaaaa aaactctgta aagttaaagg | 300 |
| aataatttga aaccaaaaat aaaaaacaat tgtattttaa cctaatagta tttaaattaa | 360 |
| aaataataat atactccgag aagaagggaa tatataagaa gagcggcgga gctaaagaag | 420 |
| agagtgggca tagtagacga gaaggagaa gaagagaatc ataagaaagc aagaaagaaa | 480 |

<210> SEQ ID NO 5
<211> LENGTH: 34
<212> TYPE: DNA
<213> ORGANISM: Artificial Sequence
<220> FEATURE:
<223> OTHER INFORMATION: Synthetic Primer

<400> SEQUENCE: 5

| | |
|---|---|
| ctccgaatat ctcttagttg aaaaaaaaca tttc | 34 |

<210> SEQ ID NO 6
<211> LENGTH: 35
<212> TYPE: DNA
<213> ORGANISM: Artificial Sequence
<220> FEATURE:
<223> OTHER INFORMATION: Synthetic Primer

<400> SEQUENCE: 6

| | |
|---|---|
| tttctttctt gctttcttat gattctcttc ttctc | 35 |

TRANSCRIPTION REGULATING NUCLEOTIDE SEQUENCES AND METHODS OF USE

CROSS-REFERENCE TO RELATED APPLICATIONS

This is the U.S. national phase of International Application No. PCT/US2021/021967, filed Mar. 11, 2021, which claims the benefit of U.S. Provisional Patent Application Nos. 62/988,238, filed on Mar. 11, 2020, and 63/116,376, filed Nov. 20, 2020.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "202017A_Seqlisting", which was created on Aug. 3, 2022 and is 5 kilobytes in size. The subject matter of the Sequence Listing is incorporated herein in its entirety by reference.

FIELD OF THE INVENTION

Described herein are nucleic acid having constitutive promoter activities and the use of such nucleic acid having constitutive promoter activities to express a polynucleotide of interest in plants.

BACKGROUND

Modification of plants to alter and/or improve phenotypic characteristics (such as productivity or quality) requires the overexpression or down-regulation of endogenous genes or the expression of heterologous genes in plant tissues. Such genetic modification relies on the availability of a means to drive and to control gene expression as required. Indeed, genetic modification relies on the availability and use of suitable promoters which are effective in plants and which regulate gene expression so as to give the desired effect(s) in the plant.

BRIEF SUMMARY

In one aspect, described herein is a recombinant gene for regulating expression of a polynucleotide of interest, said recombinant gene comprising a nucleic acid having constitutive promoter activity that is at least 80% identical to the nucleic acid sequence set forth in SEQ ID NO: 1 or SEQ ID NO: 2 or a functional fragment thereof. In some embodiments, the nucleic acid having constitutive promoter activity is at least 80% (or at least 90%, 95%, 98% or at least 99%) or more identical to the nucleotide sequence set forth in SEQ ID NO: 1 or SEQ ID NO: 2. In some embodiments, the nucleic acid having constitutive promoter activity comprises the nucleic acid sequence set forth in SEQ ID NO: 1 or SEQ ID NO: 2.

The recombinant gene in some embodiments further comprises at least one polynucleotide of interest being operatively linked to the nucleic acid having constitutive promoter activity. In some embodiments, the polynucleotide of interest is an herbicide-tolerance coding sequence, an insecticidal coding sequence, an nematicidal coding sequence, an antimicrobial coding sequence, an antifungal coding sequence, an antiviral coding sequence, an abiotic and biotic stress tolerance coding sequences, or a sequence modifying plant traits such as yield, grain quality, nutrient content, starch quality and quantity, nitrogen fixation and/or utilization, and oil content and/or composition. In some embodiments, the polynucleotide of interest is heterologous with respect to the nucleic acid having constitutive promoter activity.

In another aspect, the disclosure provides a vector comprising a recombinant gene described herein. In some embodiments, the vector is an expression vector.

In another aspect, the disclosure provides a host cell comprising a recombinant gene or vector described herein. In some embodiments, the host cell is a plant cell.

In another aspect, the disclosure provides a plant, or plant part or seed comprising a recombinant gene or a vector described herein or the heterologous nucleic acid having constitutive promoter activity described herein. In some embodiments, the plant or plant part or seed is a monocotyledonous plant or plant part. In some embodiments, the plant or plant part or seed is a dicotyledonous plant or plant part or seed. In some embodiments, the plant or plant part is hemizygous for the recombinant gene. In some embodiments, the plant or plant part is homozygous for the recombinant gene.

In another aspect, the disclosure provides a method for expressing a polynucleotide of interest in a host cell comprising (a) introducing or providing a nucleic acid having constitutive promoter activity, a recombinant gene or a vector of described herein into the host cell. In some embodiments, the host cell is a plant cell. In some embodiments, the detectable amount of protein accumulated that is encoded by the polynucleotide of interest is about 0.01%-1.15% (or about 0.05%-1.15%, or about 0.1%-1.15%, or about 0.5%-1.15%, or about 1%-1.15%) of the extracted total soluble proteins. The term "Total Soluble Protein (TSP)" as used herein refers to all proteins able to be solubilized in a buffer suitable for protein quantification typically facilitated by mechanical disruption.

In another aspect, the disclosure provides a method for producing a plant or plant part or seed comprising (a) introducing a nucleic acid having constitutive promoter activity, a recombinant gene or a vector described herein into a plant cell; and (b) regenerating a plant or plant part from said plant cell. In some embodiments, two or more copies of the recombinant gene are introduced into the plant cell.

In another aspect, the disclosure provides a method of providing pesticidal activity in a plant comprising introducing or providing the recombinant gene comprising a polynucleotide sequence that encodes a pesticidal protein into a host cell of the plant. In some embodiments, the pesticidal protein is an insecticidal protein. In some embodiments, two or more copies of the recombinant gene are introduced into the plant cell.

DETAILED DESCRIPTION

Figure 1:
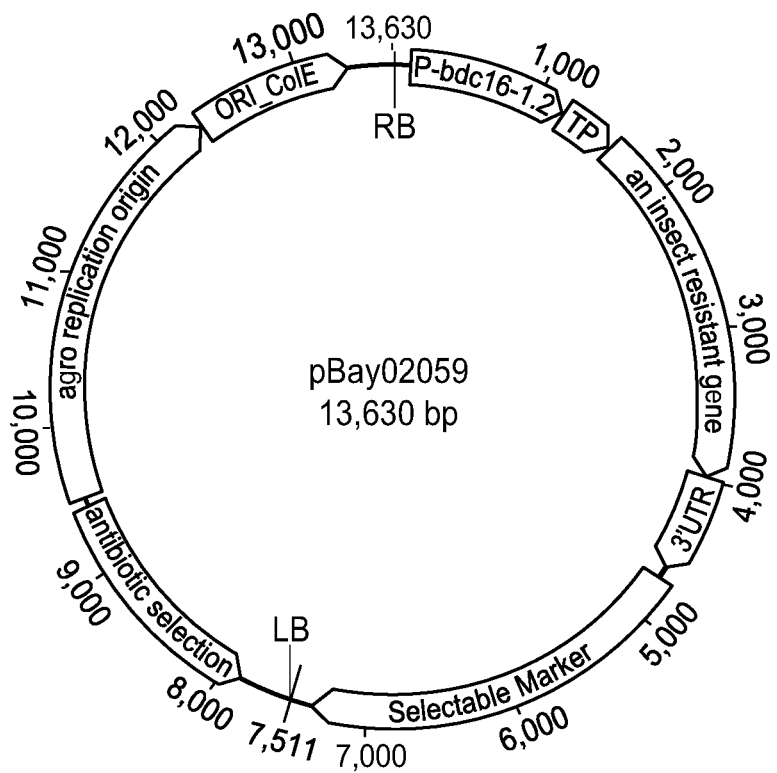
FIG. 1 depicts the components of plasmid pBay02059, including the nucleic acid having constitutive promoter activity set forth in SEQ ID NO: 1 (P-bdc16-1.2) and an insect resistant gene. Illustrates an aspect of the subject matter in accordance with one embodiment.

The present disclosure provides an isolated nucleic acid having constitutive promoter activity and a recombinant gene comprising said nucleic acid having constitutive promoter activity that directs constitutive transcription/expression of an operably linked polynucleotide of interest in a plant cell, plant, or plant part or seed. The present invention is based on the discovery that the nucleic acid having constitutive promoter activity comprising the nucleic acid sequence set forth in SEQ ID NO: 1 or SEQ ID NO: 2 and functional fragments thereof have constitutive promoter activity in plants and provides a moderate expression level of a polynucleotide of interest (e.g., polynucleotide encoding an insecticidal protein). Such moderate expression allows proteins such as insect resistant proteins/insecticidal toxins to be expressed at a level such that the protein works effectively as an insecticide without adverse effects (e.g., toxicity) to the plant.

In one aspect, described herein is a recombinant gene for regulating expression of a polynucleotide of interest, said recombinant gene comprising a nucleic acid having constitutive promoter activity that is at least 80% (or at least 90%, 95%, 98%, or at least 99%) identical to the nucleic acid sequence set forth in SEQ ID NO: 1 or SEQ ID NO: 2, or functional fragment thereof. In some embodiments, the nucleic acid having constitutive promoter activity comprises the nucleic acid sequence set forth in SEQ ID NO: 1 or SEQ ID NO: 2.

As used herein, "nucleic acid having promoter activity" refers to the nucleotide sequence of a promoter.

The term "functional fragment thereof" as used herein refers to a nucleic acid sequence that is shorter in length than the nucleic acid having constitutive promoter activity set forth in SEQ ID NO: 1 or SEQ ID NO: 2 yet retains the activity of the nucleic acid having constitutive promoter activity set forth in SEQ ID NO: 1 or SEQ ID NO: 2. For example, in some embodiments, the functional fragment of the nucleic acid having constitutive promoter activities comprises a nucleotide sequence at least 850 bp, at least 900 bp or at least 1000 bp) in length and retains the activity of the nucleic acid having constitutive promoter activity.

Expression Vectors

Another object of the present invention refers to a vector comprising the recombinant gene of the present invention.

The term "vector", encompasses phage, plasmid, viral or retroviral vectors as well as artificial chromosomes, such as bacterial or yeast artificial chromosomes. Moreover, the term also relates to targeting constructs which allow for random or site-directed integration of the targeting construct into genomic DNA. Such target constructs comprise DNA of sufficient length for either homologous or heterologous recombination as described in detail below. The vector encompassing the polynucleotides of the present invention may comprise selectable markers for propagation and/or selection in a host. The vector may be incorporated into a host cell by various techniques well known in the art. If introduced into a host cell, the vector may reside in the cytoplasm or may be incorporated into the genome. In the latter case, it is to be understood that the vector may further comprise nucleic acid sequences which allow for homologous recombination or heterologous insertion. Vectors can be introduced into prokaryotic or eukaryotic cells via conventional transformation or transfection techniques. The terms "transformation" and "transfection", conjugation and transduction, as used in the present context, are intended to comprise a multiplicity of well known in the art processes for introducing foreign nucleic acid (for example DNA) into a host cell, including calcium phosphate, rubidium chloride or calcium chloride co-precipitation, DEAE-dextran-mediated transfection, lipofection, natural competence, carbon-based clusters, chemically mediated transfer, electroporation or particle bombardment (e.g., "gene-gun"). Suitable methods for the transformation or transfection of host cells, including plant cells, can be found in Sambrook et al. (Molecular Cloning: A Laboratory Manual, 2nd ed., Cold Spring Harbor Laboratory, Cold Spring Harbor Laboratory Press, Cold Spring Harbor, NY, 1989) and other laboratory manuals, such as Methods in Molecular Biology, 1995, Vol. 44, *Agrobacterium* protocols, Ed.: Gartland and Davey, Humana Press, Totowa, New Jersey. Alternatively, a plasmid vector may be introduced by heat shock or electroporation techniques. Should the vector be a virus, it may be packaged in vitro using an appropriate packaging cell line prior to application to host cells. Retroviral vectors may be replication competent or replication defective. In the latter case, viral propagation generally will occur only in complementing hosticells.

The vector referred to herein may be suitable as a cloning vector, i.e. replicable in microbial systems. Such vectors ensure efficient cloning in bacteria, yeasts or fungi and make possible the stable transformation of plants. Those which must be mentioned are, in particular, various binary and co-integrated vector systems which are suitable for the T DNA-mediated transformation. Such vector systems are, as a rule, characterized in that they contain at least the vir genes, which are required for the *Agrobacterium*-mediated transformation, and the sequences which delimit the T-DNA (T-DNA border). These vector systems may also comprise further cis-regulatory regions such as promoters and terminators and/or selection markers with which suitable transformed host cells or organisms can be identified. While co-integrated vector systems have vir genes and T DNA sequences arranged on the same vector, binary systems are based on at least two vectors, one of which bears vir genes, but no T-DNA, while a second one bears T DNA, but no vir gene. As a consequence, the last-mentioned vectors are relatively small, easy to manipulate and can be replicated both in *E. coli* and in *Agrobacterium*. An overview of binary vectors and their use can be found in Heliens et al, Trends in Plant Science (2000) 5, 446-451. Furthermore, by using appropriate cloning vectors, the recombinant gene of the invention can be introduced into host cells or organisms such as plants or animals and, thus, be used in the transformation of plants, such as those which are published, and cited, in: Plant Molecular Biology and Biotechnology (CRC Press, Boca Raton, Florida), chapter 6/7, pp. 71-119 (1993); F. F. White, Vectors for Gene Transfer in Higher Plants; in: Transgenic Plants, vol. 1, Engineering and Utilization, Ed.: Kung and R. Wu, Academic Press, 1993, 15-38; B. Jenes et al.; Techniques for Gene Transfer, in: Transgenic Plants, vol. 1, Engineering and Utilization, Ed.: Kung and R. Wu, Academic Press (1993), 128-143; Potrykus, Annu, Rev. Plant Physiol, Plant Molec. Biol. 42 (1991), 205 225.

The vector of the present invention may be an expression vector. In such an expression vector, the recombinant gene comprises a nucleic acid having constitutive promoter activity as specified above allowing for expression in eukaryotic cells or isolated fractions thereof. An expression vector may, in addition to the recombinant gene of the invention, also comprise further regulatory elements including transcriptional as well as translational enhancers. The expression vector may also be a gene transfer or targeting vector. Expression vectors derived from viruses such as retroviruses, vaccinia virus, adeno-associated virus, herpes viruses, or bovine papilloma virus, may be used for delivery of the recombinant genes or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994).

Suitable expression vector backbones may be derived from expression vectors known in the art such as Okayama-Berg cONA expression vector pcDV1 (Pharmacia), pCDM8, pRc/CMV, pcDNA1, pcDNA3 (Invitrogene) or pSPORT1 (GIBCO BRL). Further examples of typical fusion expression vectors are pGEX (Pharmacia Biotech Inc; Smith, D. B., and Johnson, K. S. (1988) Gene 67:31-40), pMAL (New England Biolabs, Beverly, MA) and pR115 (Pharmacia, Piscataway, NJ), where glutathione S-transferase (GST), maltose E-binding protein and protein A, respectively, are fused with the nucleic acid of interest encoding a protein to be expressed. The target gene expression of the pTrc vector is based on the transcription from a hybrid trp-lac fusion promoter by host RNA polymerase. The target gene expression from the pET 11d vector is based on the transcription of a T7-gn10-lac fusion promoter, which is mediated by a coexpressed viral RNA polymerase (T7 gn1). This viral polymerase is provided by the host strains BL21 (DE3) or HMS174 (DE3) from a resident 1-prophage which harbors a T7 gn1 gene under the transcriptional control of the lacUV 5 promoter. Examples of vectors for expression in the yeast *S. cerevisiae* comprise pYepSecl (Baldari et al. (1987) Embo J. 6:229-234), pMFa (Kurjan and Herskowitz (1982) Cell 30:933-943). pJRY88 (Schultz et al (1987) Gene 54:113-123) and pYES2 (thvitrogen Corporation, San Diego, CA), Vectors and processes for the construction of vectors which are suitable for use in other fungi, such as the filamentous fungi, comprise those which are described in detail in: van den Handel, C. A. M. J. J., & Punt, P. J. (1991) "Gene transfer systems and vector development for filamentous fungi, in: Applied Molecular Genetics of fungi, J. F. Peberdy et al., Ed., pp. 1-28, Cambridge University Press: Cambridge, or in: More Gene Manipulations in Fungi (J. W. Bennett & L. L. Lasure, Ed., pp. 396-428; Academic Press: San Diego). Further suitable yeast vectors are, for example, pAG-1, YEp6, YEp13 or pEMBLYe23.

In some embodiments, the vector (or vectors) described herein comprising the recombinant gene are propagated and amplified in a suitable organism, i.e expression host. In some embodiments, one copy of the vector is propagated and amplified in a suitable organism. In some embodiments, two or more (e.g., 3, 4, 5, 6 7, 8 or more) copies of the vector are propagated and amplified in a suitable organism.

The term "recombinant gene" as used herein refers to a linear or circular nucleic acid molecule. It encompasses DNA as well as RNA sequences which are capable of directing expression of a particular nucleotide sequence in an appropriate host cell. In general, it comprises a promoter operably linked to a polynucleotide of interest, which is—optionally—operably linked to termination signals and/or other regulatory elements. The recombinant gene of the present invention is characterized in that it shall comprise a nucleic acid having constitutive promoter activity as defined herein. A recombinant gene may also comprise sequences which may be needed for proper translation of the nucleotide sequence. The coding region usually codes for a protein of interest but may also code for a functional RNA of interest, for example antisense RNA or a non-translated RNA, in the sense or antisense direction. The recombinant gene comprising the polynucleotide sequence of interest may be chimeric, meaning that at least one of its components is heterologous with respect to at least one of its other components. The recombinant gene may also be one which is naturally occurring but has been obtained in a recombinant form useful for heterologous expression. A recombinant gene may be assembled entirely extracellularly (e.g., by recombinant cloning techniques). However, a recombinant gene may also be assembled using in part endogenous components. For example, a recombinant gene may be obtained by placing (or inserting) a promoter sequence upstream of an endogenous sequence, which thereby becomes functionally linked and controlled by said promoter sequences. Likewise, a nucleic acid sequence to be expressed may be placed (or inserted) downstream of an endogenous promoter sequence thereby forming a recombinant gene. In another embodiment, such recombinant genes will comprise a transcriptional initiation region linked to a nucleotide sequence of interest. Such a recombinant gene may be provided with a plurality of restriction sites for insertion of the gene of interest to be under the transcriptional regulation of the regulatory regions. The recombinant gene may additionally contain selectable marker genes. The cassette will include in the 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens*, such as the octopine synthase and nopaline synthase termination regions and others described below (see also, Guerineau 1991; Proudfoot 1991; Sanfacon 1991; Mogen 1990; Munroe 1990 Belles 1989; Joshi 1987). The recombinant gene can also comprise a multiple cloning site. In such a case, the multiple cloning site may be arranged in a manner as to allow for operative linkage of a polynucleotide to be introduced in the multiple cloning site with the transcription regulating sequence. In addition to the aforementioned components, the recombinant gene of the present invention may comprise components required for homologous recombination, i.e. flanking genomic sequences from a target locus. However, also contemplated is a recombinant gene which essentially consists of the nucleic acid having constitutive promoter activity, as defined hereinafter.

The terms "operably-linked" or "functionally linked" refer to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter), Coding sequences can be operably-linked to regulatory sequences in sense or antisense orientation.

The term "promoter" as used herein refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised, in some cases, of a TATA box and other sequences that serve to specify the site of transcription initiation, to which regulatory elements are added for enhancement of expression, "Promoter" also refers to a nucleotide sequence that includes a minimal promoter plus regulatory elements and that is capable of controlling the expression of a coding sequence or functional RNA. This type of promoter sequence consists of proximal and more distal upstream elements, the latter elements often referred to as enhancers. Accordingly, an "enhancer" is a DNA sequence, which can stimulate promoter activity and may be an innate element of the promoter or a heterologous element inserted to enhance the level or tissue specificity of a promoter. It is capable of operating in both orientations (normal or flipped) and, is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements, derived from different promoters found in nature, or even be comprised of synthetic DNA segments.

A promoter may also contain DNA sequences that are involved in the binding of protein factors, which control the effectiveness of transcription initiation in response to physiological or developmental conditions. The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5 direction) are denominated negative. Promoter elements, such as a TATA element, that are inactive or have greatly reduced promoter activity in the absence of upstream activation are referred as "minimal" or "core" promoters. In the presence of a suitable transcription factor, the minimal promoter functions to permit transcription. A "minimal" or "core" promoter thus consists only of all basal elements needed for transcription initiation, e.g., a TATA box and/or an initiator.

The term "constitutive promoter" as used herein refers to a promoter that is able to express the open reading frame (ORF) in all or nearly all of the plant tissues during all or nearly all developmental stages of the plant. Each of the transcription-activating elements do not exhibit an absolute tissue-specificity, but mediate transcriptional activation in most plant tissues at a level of at least 1% reached in the plant tissue in which transcription is most active. "Constitutive expression" refers to expression using a constitutive promoter.

As used herein, the term "cis-regulatory element" or "promoter motif" refers to a cis-acting transcriptional regulatory element that confers an aspect of the overall control of gene expression. A cis-element may function to bind transcription factors, trans-acting protein factors that regulate transcription, Some cis-elements bind more than one transcription factor, and transcription factors may interact in different affinities with more than one cis-element. The promoters of the present invention desirably contain cis-elements that can confer or modulate gene expression. Cis-elements can be identified by a number of techniques, including deletion analysis, i.e., deleting one or more nucleotides from the 5' end or internal of a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis with known cis-element motifs by conventional DNA sequence comparison methods. The fine structure of a cis-element can be further studied by mutagenesis (or substitution) of one or more nucleotides or by other conventional methods. Cis-elements can be obtained by chemical synthesis or by isolation from promoters that include such elements, and they can be synthesized with additional flanking nucleotides that contain useful restriction enzyme sites to facilitate subsequence manipulation.

The term "heterologous" with respect to a nucleic acid molecule or DNA refers to a nucleic acid molecule which is operably linked to, or is manipulated to become operably linked to, a second nucleic acid molecule to which it is not operably linked in nature, or to which it is operably linked at a different location in nature. For example, a promoter of the invention is in its natural environment functionally linked to its native coding sequence, whereas in the present invention it is linked to another coding sequence which might be derived from the same organism, a different organism or a synthetic coding sequence. It is in addition to be understood that the coding sequence under the control of the promoter of the invention is heterologous to said promoter as its sequence has been manipulated, by for example mutation such as insertions, deletions and the forth so that the natural sequence of said coding sequence is modified and therefore have become heterologous to a promoter of the invention. Furthermore, the nucleic acid having constitutive promoter activity is heterologous to the plant, plant part or seed comprising it if it is synthetic, derived from another non-crossable organism (transgenic), another crossable organism (cisgenic) or the same organism but its natural genomic localization is rendered compared to a control plant (cisgenic), for example a wild type plant. It is to be understood, that a rendered genomic localization means the nucleic acid having constitutive promoter activity is located, on another chromosome or on the same chromosome but 10 kb or more, for example 10 kb, preferably 5 kb or more, for example 5 kb, more preferably 1000 bp or more, for example 1000 bp, even more preferably 500 bp or more, for example 500 bp, especially preferably 100 bp or more, for example 100 bp, most preferably 10 bp or more, for example 10 bp dislocated from its natural genomic localization in a wild type plant.

Expression in a Host Ceil

In another aspect, described herein is a method for expressing a polynucleotide of interest in a host cell comprising introducing a recombinant gene or vector described herein into the host cell and expressing the polynucleotide of interest in the host cell.

The term "expression" as used herein refers to the transcription and/or translation of an endogenous gene, ORF or portion thereof, a transgene or cisgene in plants. For example, in the case of antisense constructs, expression may refer to the transcription of the antisense DNA only. In addition, expression refers to the transcription and stable accumulation of sense (mRNA) or functional RNA. Expression may also refer to the production of protein.

The "expression pattern" of a promoter (with or without enhancer) is the pattern of expression levels, which shows where in the plant and in what developmental stage transcription is initiated by said promoter. Expression patterns of a set of promoters are said to be complementary when the expression pattern of one promoter shows little overlap with the expression pattern of the other promoter. The level of expression of a promoter can be determined by measuring the 'steady state' concentration of a standard transcribed reporter mRNA. This measurement is indirect since the concentration of the reporter mRNA is dependent not only on its synthesis rate, but also on the rate with which the mRNA is degraded, Therefore, the steady state level is the product of synthesis rates and degradation rates. The rate of degradation can however be considered to proceed at a fixed rate when the transcribed sequences are identical, and thus this value can serve as a measure of synthesis rates. When promoters are compared in this way, techniques available to those skilled in the art are hybridization S1-RNAse analysis, northern blots and competitive RT-PCR. This list of techniques in no way represents all available techniques, but rather describes commonly used procedures used to analyze transcription activity and expression levels of mRNA. The analysis of transcription start points in practically all promoters has revealed that there is usually no single base at which transcription starts, but rather a more or less clustered set of initiation sites, each of which accounts for some start points of the mRNA. Since this distribution varies from promoter to promoter the sequences of the reporter mRNA in each of the populations would differ from each other. Since each mRNA species is more or less prone to degradation, no single degradation rate can be expected for different reporter mRNAs. It has been shown for various eukaryotic promoter sequences that the sequence surrounding the initiation site ('initiator') plays an important role in determining the level of RNA expression directed by that specific promoter. This includes also part of the transcribed sequences. The direct fusion of promoter to reporter sequences would therefore lead to suboptimal levels of transcription. A commonly used procedure to analyze expression patterns and levels is through determination of the 'steady state' level of protein accumulation in a cell. Commonly used candidates for the reporter gene, known to those skilled in the art are beta-glucuronidase (GUS), chloramphenicol acetyl transferase (CAT) and proteins with fluorescent properties, such as green fluorescent protein (GFP) from *Aequorea victoria*. In principle, however, many more proteins are suitable for this purpose, provided the protein does not interfere with essential plant functions. For quantification and determination of localization a number of tools are suited. Detection systems can readily be created or are available which are based on, e.g., immunochemical, enzymatic, fluorescent detection and quantification. Protein levels can be determined in plant tissue extracts or in intact tissue using in situ analysis of protein expression. Generally, individual transformed lines with one chimeric promoter reporter construct may vary in their levels of expression of the reporter gene. Also frequently observed is the phenomenon that such transformants do not express any detectable product (RNA or protein). The variability in expression is commonly ascribed to 'position effects', although the molecular mechanisms underlying this inactivity are usually not clear.

The expression of the polynucleotide of interest can be determined by various well known techniques, e.g., by Northern Blot or in situ hybridization techniques as described in WO 02/102970.

Nucleic Acids

The term "nucleic acid" as used herein refers to deoxyribonucleotides or ribonucleotides and their polymers thereof in either single- or double-stranded form, composed of monomers (nucleotides) containing a sugar, phosphate and a base, which is either a purine or pyrimidine. Unless specifically limited, the term encompasses nucleic acids containing known analogs of natural nucleotides, which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer 1991; Ohtsuka 1985; Rossolini 1994). A "nucleic acid fragment" is a fraction of a given nucleic acid molecule. In higher plants, deoxyribonucleic acid (DNA) is the genetic material while ribonucleic acid (RNA) is involved in the transfer of information contained within DNA into proteins. The term "nucleotide sequence" refers to a polymer of DNA or RNA which can be single- or double-stranded, optionally containing synthetic, non-natural or altered nucleotide bases capable of incorporation into DNA or RNA polymers. The terms "nucleic acid" or "nucleic acid sequence" may also be used interchangeably with gene, cDNA, DNA and RNA encoded by a gene.

"Isolated nucleic acid", used interchangeably with "isolated DNA" as used herein refers to a nucleic acid not occurring in its natural genomic context, irrespective of its length and sequence. Isolated DNA can, for example, refer to DNA which is physically separated from the genomic context, such as a fragment of genomic DNA. Isolated DNA can also be an artificially produced DNA, such as a chemically synthesized DNA, or such as DNA produced via amplification reactions, such as polymerase chain reaction (PCR) well-known in the art. Isolated DNA can further refer to DNA present in a context of DNA in which it does not occur naturally. For example, isolated DNA can refer to a piece of DNA present in a plasmid. Further, the isolated DNA can refer to a piece of DNA present in another chromosomal context than the context in which it occurs naturally, such as for example at another position in the genome than the natural position, in the genome of another species than the species in which it occurs naturally, or in an artificial chromosome.

Nucleic acid variants of the nucleic acid having constitutive promoter activity that retain the activity of the wild-type nucleic acid having constitutive promoter activity are also contemplated. The term "variant" as used herein with respect to a sequence (e.g., a polypeptide or nucleic acid sequence such as—for example—a nucleic acid having constitutive promoter activity of the invention) is intended to mean substantially similar sequences. Naturally occurring allelic variants such as these can be identified with the use of well-known molecular biology techniques, as, for example, with polymerase chain reaction (PCR) and hybridization techniques.

Variant nucleotide sequences also include synthetically derived nucleotide sequences, such as those generated, for example, by using site-directed mutagenesis. Generally, nucleotide sequence variants of the invention will have at least 70%, e.g., 71%, 72%, 73%, 74%, 75%, 76%, 77%, 78%, to 79%, generally at least 80%, e.g., 81%-84%, at least 85%, e.g., 86%, 87%, 88%, 89% 90%, 91%, 92%, 93%, 94%, 95%, 96%, 97%, to 98% and 99% nucleotide sequence identity to the native (wild type or endogenous) nucleotide sequence set forth in SEQ ID NO: 1 or SEQ ID NO: 2 or a functional fragment thereof.

As used herein, the term "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity, Thus, for example, where an identical amino acid is given a score of 1 and a non-conservative substitution is given a score of zero, a conservative substitution is given a score between zero and 1, The scoring of conservative substitutions is calculated, e.g., as implemented in the program PC/GENE (Intelligenetics, Mountain View, Calif.).

The term "substantial identity" of polynucleotide sequences means that a polynucleotide comprises a sequence that has at least 70%, 71%, 72%, 73%, 74%, 75%, 76%, 77%, 78%, or 79%, at least 80%, 81%, 82%, 83%, 84% 85%, 86%, 87%, 88%, or 89%, at least 90%, 91%, 92%, 93%, or 94%, and at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

Another indication that nucleotide sequences are substantially identical is if two molecules hybridize to each other under stringent conditions (see below). Generally, stringent conditions are selected to be about 5° C. lower than the thermal melting point (Tin) for the specific sequence at a defined ionic strength and pH. However, stringent conditions encompass temperatures in the range of about 1° C. to about 20° C., depending upon the desired degree of stringency as otherwise qualified herein, Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

Stringent hybridization conditions" and "stringent hybridization wash conditions" in the context of nucleic acid hybridization experiments such as Southern and Northern hybridization are sequence dependent and are different under different environmental parameters. The Tm is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the Tm can be approximated from the equation of Meinkoth and Wahl, 1984:

$$Tm = 81.5° C. + 16.6(\log 10\, M) + 0.41\, (\% GC) - 0.61\, M\, form) - 500/L$$

where M is the molarity of monovalent cations, % GC is the percentage of guanosine and cytosine nucleotides in the DNA, % form is the percentage of formamide in the hybridization solution, and L is the length of the hybrid in base pairs. Tm is reduced by about 1° C. for each 1% of mismatching; thus, Tm, hybridization, and; or wash conditions can be adjusted to hybridize to sequences of the desired identity. For example, if sequences with >90% identity are sought, the Tri can be decreased 10° C. Generally, stringent conditions are selected to be about 5° C. lower than the thermal melting point I for the specific sequence and its complement at a defined ionic strength and pH. However, severely stringent conditions can utilize a hybridization and/or wash at 1, 2, 3, or 4° C. lower than the thermal melting point I; moderately stringent conditions can utilize a hybridization and/or wash at 6, 7, 8, 9, or 10° C. lower than the thermal melting point I; low stringency conditions can utilize a hybridization and/or wash at 11, 12, 13, 14, 15, or 20° C. lower than the thermal melting point I. Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of nucleic acids is found in Tijssen, 1993. Generally, highly stringent hybridization and wash conditions are selected to be about 5° C. lower than the thermal melting point Tm for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see. Sambrook, infra, for a description of SSC buffer), Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4 to 6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long robes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the Tm for a particular probe. An example of highly stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37'C, and a wash in 0.5× to 1×SSC at 55 to 60° C.

The following are examples of sets of hybridization/wash conditions that may be used to clone nucleotide sequences that are substantially identical to reference nucleotide sequences of the present invention: a reference nucleotide sequence preferably hybridizes to the reference nucleotide sequence in 7% sodium dodecyl sulfate (SOS), 0.5 M NaPO4, 1 mM EDTA at 50° C. with washing in 2×SSC, 0.1% SDS at 50° C. (very low stringency conditions), more desirably in 7% sodium dodecyl sulfate (SOS), 0.5 M NaPO4, 1 mM EDTA at 50° C. with washing in 1×SSC, 0_1% SOS at 50° C. (low stringency conditions), more desirably still in 7% sodium dodecyl sulfate (SOS), 0.5 M NaPO4, 1 mM EDTA at 50° C. with washing in 0.5×SSC, 0.1% SOS at 50° C. (moderate stringency conditions), preferably in 7% sodium dodecyl sulfate (SOS), 0.5 M NaPO4, 1 mM EDTA at 50° C. with washing in 0.1×SSC, 0.1% SOS at 50° C. (high stringency conditions), more preferably in 7% sodium dodecyl sulfate (SOS), 0.5 M NaPO4, 1 mM EDTA at 50° C. with washing in 0.1×SSC, 0.1% SOS at 65° C. (very high stringency conditions).

In some embodiments, the nucleic acid molecules described herein can be "optimized" for enhanced expression in plants of interest (see, for example, WO 91/16432; Perlak 1991; Murray 1989). In this manner, the open reading frames in genes or gene fragments can be synthesized utilizing plant-preferred codons (see, for example, Campbell & Gowri, 1990 for a discussion of host-preferred codon usage). Thus, the nucleotide sequences can be optimized for expression in any plant. It is recognized that all or any part of the gene sequence may be optimized or synthetic. That is, synthetic or partially optimized sequences may also be used. Variant nucleotide sequences and proteins also encompass sequences and protein derived from a mutagenic and recombinogenic procedure such as DNA shuffling. With such a procedure, one or more different coding sequences can be manipulated to create a new polypeptide possessing the desired properties, in this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art (see, for example, Stemmer 1994; Stemmer 1994; Crameri 1997; Moore 1997; Zhang 1997; Crameri 1998; and U.S. Pat. No. 5,605,794, 6, 8, 10, and U.S. Pat. No. 12,837,458).

Polynucleotides of Interest

The term "polynucleotide of interest" as used herein refers to a nucleic acid which is expressed under the control of the nucleic acid having constitutive promoter activity referred to herein. A polynucleotide of interest may encode a polypeptide the presence of which is desired in a plant cell, a plant, or a plant part as referred to herein. Such a polypeptide may be an enzyme which is required for the synthesis of seed storage compounds or may be a seed storage protein. It is to be understood that if the polynucleotide of interest encodes a polypeptide, transcription of the nucleic acid in RNA and translation of the transcribed RNA into the polypeptide may be required. A polynucleotide of interest may also include biologically active RNA molecules and antisense RNAs, ribozymes, micro RNAs or siRNAs. For example, an undesired enzymatic activity in a seed can be reduced due to the seed specific expression of an antisense RNAs, ribozymes, micro RNAs or siRNAs. The underlying biological principles of action of the aforementioned biologically active RNA molecules are well known in the art. Moreover, the person skilled in the art is well aware of how to obtain nucleic acids which encode such biologically active RNA molecules. It is to be understood that the biologically active RNA molecules may be directly obtained by transcription of the nucleic acid of interest, i.e. without translation into a polypeptide, Preferably, at least one polynucleotide of interest to be expressed under the control of the nucleic acid having constitutive promoter activity of the present invention is heterologous in relation to said the nucleic acid having constitutive promoter activity, i.e. it is not naturally under the control thereof, but said control has been produced in a non-natural manner (for example by genetic engineering processes)

An operable linkage in relation to any recombinant gene described herein may be realized by various methods known in the art, comprising both in vitro and in vivo procedure. Thus, a recombinant gene of the invention or an vector comprising such recombinant gene may by realized using standard recombination and cloning techniques well known in the art (see e.g., Maniatis 1989; Silhavy 1984; Ausubel 1987).

An operable linkage may—for example—comprise a sequential arrangement of the nucleic acid having constitutive promoter activity described herein (for example, the nucleotide sequence set forth in SEQ ID NO: 1 or SEQ ID NO: 2, or functional fragment thereof) with a nucleic acid sequence to be expressed, and—optionally—additional regulatory elements such as for example polyadenylation or transcription termination elements, enhancers, introns, etc, in a way that the nucleic acid having constitutive promoter activity can fulfill its function in the process of expressing the nucleic acid sequence of interest under the appropriate conditions. The term "appropriate conditions" may mean the presence of the recombinant gene in a plant cell. Preferred are arrangements, in which the nucleic acid sequence of interest to be expressed is placed down-stream (i.e., in 3'-direction) of the nucleic acid having constitutive promoter activity of the invention in a way, that both sequences are covalently linked. Optionally additional sequences may be inserted in-between the two sequences. Such sequences may be for example linker or multiple cloning sites. Furthermore, sequences can be inserted coding for parts of fusion proteins (in case a fusion protein of the protein encoded by the nucleic acid of interest is intended to be expressed). Preferably, the distance between the polynucleotide of interest to be expressed and the nucleic acid having constitutive promoter activity of the invention is not more than 200 base pairs, preferably not more than 100 base pairs, more preferably no more than 50 base pairs.

In some embodiments, a recombinant gene is assembled by inserting a nucleic acid having constitutive promoter activity described herein (for example a nucleotide sequence set forth in SEQ ID NO: 1 or SEQ ID NO: 2, or functional fragment thereof) into the plant genome. Such insertion will result in an operable linkage to a nucleic acid sequence of interest, which as such already existed in the genome. By the insertion, the nucleic acid of interest is expressed in a constitutive way due to the transcription regulating properties of the nucleic acid having constitutive promoter activity. The insertion may be directed or by chance. When the insertion is directed, it may be realized by for example gene editing. By this procedure a natural promoter may be exchanged against the nucleic acid having constitutive promoter activity of the invention, thereby modifying the expression profile of an endogenous gene. The nucleic acid having constitutive promoter activity may also be inserted in a way, that antisense mRNA of an endogenous gene is expressed, thereby inducing gene silencing.

Similarly, a polynucleotide of interest to be expressed may by inserted into a plant genome comprising the nucleic acid having constitutive promoter activity in its natural genomic environment (i.e. linked to its natural gene) in a way that the inserted sequence becomes operably linked to the nucleic acid having constitutive promoter activity, thereby forming a recombinant gene of the invention.

The recombinant gene may be employed for numerous expression purposes such as for example expression of a protein, or expression of an antisense RNA, sense or double-stranded RNA. Expression of the nucleic acid sequence may confer to the plant an agronomically valuable trait.

In some embodiments, the polynucleotide of interest is obtained from an insect resistance gene; a disease resistance gene such as, for example, a bacterial disease resistance gene, a fungal disease resistance gene, a viral disease resistance gene, or a nematode disease resistance gene; a herbicide resistance gene; a gene affecting grain composition or quality; a nutrient utilization gene; a mycotoxin reduction gene; a male sterility gene; a selectable marker gene; a screenable marker gene; a negative selectable marker; a positive selectable marker; a gene affecting plant agronomic characteristics, i.e yield, standability, and the like; or an environment or stress resistance gene, i.e., one or more genes that confer herbicide resistance or tolerance, insect resistance or tolerance, disease resistance or tolerance (viral, bacterial, fungal, oomycete, or nematode), stress tolerance or resistance (as exemplified by resistance or tolerance to drought, heat, chilling, freezing, excessive moisture, salt stress, or oxidative stress), increased yields, food content and makeup, physical appearance, male sterility, drydown, standability, prolificacy, starch properties or quantity, oil quantity and quality, amino acid or protein composition, and the like.

By "resistant" is meant a plant, which exhibits substantially no phenotypic changes as a consequence of agent administration, infection with a pathogen, or exposure to stress, By "tolerant" is meant a plant, which, although it may exhibit some phenotypic changes as a consequence of infection, does not have a substantially decreased reproductive capacity or substantially altered metabolism.

In some embodiments, the polynucleotide of interest is a selectable marker gene. The term "selectable marker gene" as used herein, refers to a gene that—in the presence of the corresponding selection compound (e.g., herbicide) in the growing medium—confers a growth advantage to a plant or plant cell transformed with a plant recombinant gene for said selectable marker as compared to a plant or plant cell not been transformed with said plant recombinant gene and which, thus, does not comprise the selectable marker gene. The selectable marker gene and/or plant recombinant gene for said marker gene may be heterologous to the plant to be transformed, and thus is not naturally present in the plant to be transformed.

In some embodiments, the selectable marker gene is a negative selection marker gene. Negative selection marker genes confer a resistance and/or increased tolerance to a selection compound (e.g., herbicide). Exemplary selectable marker genes include, but are not limited to, HPPD inhibitors as described in WO/2011/095460, incorporated herein by reference in its entirety; Phosphinothricin acetyltransferases (PAT; also named Bialaphoeresistance; bar; De Block et al. (1987) Plant Physiol 91:694-701; EP 0 333 033; U.S. Pat. No. 4,975,374) 5-enolpyruvyishikimate-3-phosphate synthase (EPSPS; U.S. Pat. No. 5,633,435) or glyphosate oxidoreduotase gene (U.S. Pat. No. 5,463,175) conferring resistance to Glyphosate™ (N-(phosphonomethyl)glycine) (Shah of al. (1986) Science 233: 478) Glyphosate™ degrading enzymes (Glyphosate™ oxidoreductase; gox), Sulfonylurea- and imidazolinone-inactivating acetolactate synthases (for example mutated ALS variants with, for example, the S4 and/or Hra mutation Bromoxynil™ degrading nitrilases (bxn) Kanamycin- or, G418-resistance genes (NPTII; NPTI) coding e.g., for neomycin phosphotransferases (Fraley et al. (1983) Proc Natl Acad Sci USA 80:4803), which expresses an enzyme conferring resistance to the antibiotic kanamycin and the related antibiotics neomycin, paromomycin, gentamicin, and G418. Dicamba degrading enzymes (O-demethylase, oxygenase, ferredoxin) (Behrens et al. 2007 Science 316:1185-1188; U.S. Pat. No. 7,022,896) marker genes that confer resistance against the toxic effects imposed by D-amino acids like e.g., D-alanine and D-serine (WO03/060133). Marker genes in this contest may be, the daol gene (EC: 1.4. 3.3: GenBank Acc.-No. U60066) from the yeast *Rhodotorula gracilis* (*Rhodosporidium toruloides*) and the *E. coli* gene dsdA (D-serine dehydratase (D-serine deaminase) [EC: 4.3. 1.18; GenBank Acc.-No.: J01603).

In some embodiments, the selectable marker gene is a positive selection marker, which confers a growth advantage to a transformed plant in comparison with a non-transformed one. Exemplary positive selection markers include, but are not limited to, mannose-6-phosphate isomerase (in combination with mannose), UDPgalactose-4-epimerase (in combination with e.g., galactose), or mannose-6-phosphate isomerase in combination with mannose.

In some embodiments, the selectable marker gene is the acetohydroxy acid synthase (AHAS) gene, or a mutated AHAS gene. The acetohydroxy acid synthase enzyme (also known as acetolactate synthase, or ALS) is a protein found in plants and microorganisms and which catalyzes the first step in the synthesis of the branched-chain amino acids (valine, leucine, and isoleucine). Preferably, it has enzymatic activity as set forth in the Enzyme Commission Code EC 2.2.1.6. The mutated AHAS protein, preferably, confers resistance to at least one imidazolinone herbicide. Imidazolinone herbicides are well known in the art, and, preferably, include imazapyr, imazaquin, imazethapyr, imazapic, imazamox and imazamethabenz. Preferably, the imidazolinone herbicide is imazaquin. More preferably, the imidazolinone herbicide is imazethapyr. Most preferably, the imidazolinone herbicide is imazapyr.

Exemplary mutated AHAS genes are disclosed in WO2004/005516 or WO2008/124495 which herewith is incorporated by reference with respect to its entire disclosure content. Further mutated AHAS genes are disclosed in WO2006/015376 or WO2007/054555 or 0520100287641. The mutated AHAS enzyme confers resistance to imidazolinone herbicides.

Further selection marker genes are marker genes that confer resistance or increased tolerance to the toxic effects imposed by D-amino acids. Such marker genes may encode for proteins which are capable of metabolizing D-amino acids. D-amino acids may be D-alanine and D-serine. Marker genes may encode for D-serine ammonialyases, D-amino acid oxidases and D-alanine transaminases. Preferred examples for such marker genes encoding for proteins which are capable of metabolizing D-amino acids are those which are as disclosed in International Patent Publication Nos. WO 03/060133, WO 05/090584, WO 07/107,516 and WO 08/077,570 which are incorporated herein by reference in their entirety.

In some embodiments, the polynucleotide of interest in a herbicide resistant gene encoding a herbicide resistant protein. Exemplary herbicide resistant genes include, but are not limited to the genes encoding phosphinothricin acetyltransferase (bar and pat), glyphosate tolerant EPSP synthase genes, the glyphosate degradative enzyme gene gox encoding glyphosate oxidoreductase, deh (encoding a dehalogenase enzyme that inactivates dalapon), herbicide resistant (e.g., sulfonylurea and imidazolinone) acetolactate synthase, and bxn genes (encoding a nitrilase enzyme that degrades bromoxynil). The bar and pat genes code for an enzyme, phosphinothricin acetyltransferase (PAT), which inactivates the herbicide phosphinothricin and prevents this compound from inhibiting glutamine synthetase enzymes. The enzyme 5-enolpyruvylshikimate 3-phosphate synthase (EPSP Synthase), is normally inhibited by the herbicide N-(phosphonomethyl)glycine (glyphosate). However, genes are known that encode glyphosate-resistant EPSP Synthase enzymes. The deh gene encodes the enzyme dalapon dehalogenase and confers resistance to the herbicide dalapon. The bxn gene codes for a specific nitrilase enzyme that converts bromoxynil to a non-herbicidal degradation product.

In some embodiments, the polynucleotide of interest is an insect resistant gene or a variant thereof encoding an insect resistant protein, Such variants can include synthetically derived sequences including but not limited to sequences that are a fusion of two or more polynucleotides of interest (e.g., two or more insect resistant genes).

Exemplary insect resistant genes include, but are not limited to, genes that encode insecticidal proteins such as the Cry and Cyt proteins as well as genes that encode insecticidal proteins such as the vegetative insecticidal proteins known as the "Vip" proteins, all of which are well known to persons of skill in the art. Examples of such genes include Cry1, such as members of the Cry1A, Cry1B, Cry1C, Cry1D, Cry1E, Cry1F, and Cr1I families; Cry2, such as members of the Cry2A family; Cry9, such as members of the Cry9A. Cry9B, Cry9C, Cry9D, Cry9E, and Cry9F families; and members of the Vip3 family, etc. It will be understood by one of skill in the art that the plant may comprise any gene imparting an agronomic trait of interest. Exemplary insect resistant genes include, but are not limited to, *Bacillus thuringiensis* crystal toxin genes or Bt genes (Watrud 1985). Bt genes may provide resistance to lepithopteran or coleopteran pests such as European Corn Borer (ECB) and corn rootworm (CRW), Bt toxin genes for use in such embodiments may include the Cry1A(b) and Cry1A(c) genes, Endotoxin genes from other species of B, *thuringiensis*, which affect insect growth or development, may also be employed in this regard. Protease inhibitors may also provide insect resistance (Johnson 1989), and will thus have utility in plant transformation. The use of a protease inhibitor II gene, pinII, from tomato or potato is envisioned to be particularly useful. Other genes, which encode inhibitors of the insects' digestive system, or those that encode enzymes or co-factors that facilitate the production of inhibitors, may also be useful. Cystatin and amylase inhibitors, such as those from wheat and barley, may exemplify this group.

Also, genes encoding lectins may confer additional or alternative insecticide properties. Lectins (originally termed phytohemagglutinins) are multivalent carbohydrate binding proteins, which have the ability to agglutinate red blood cells from a range of species, Lectins have been identified recently as insecticidal agents with activity against weevils, ECB and rootworm (Murdock 1990; Czapla & Lang, 1990). Lectin genes contemplated to be useful include, for example, barley and wheat germ agglutinin (WGA) and rice lectins (Gatehouse 1984), with WGA being preferred.

Genes controlling the production of large or small polypeptides active against insects when introduced into the insect pests, such as, e.g., lytic peptides, peptide hormones and toxins and venoms, form another aspect of the invention. For example, it is contemplated, that the expression of juvenile hormone esterase, directed towards specific insect pests, may also result in insecticidal activity, or perhaps cause cessation of metamorphosis (Hammock 1990).

Plants and Host Cells

Host cells or non-human, organisms comprising a recombinant gene described herein are also contemplated. They may be prokaryotic or eukaryotic organisms. Both microorganism and higher organisms are comprised, Examples of microorganisms are bacteria, yeast, algae, and fungi. Preferred bacteria are those of the genus *Escherichia, Erwinia, Agrobacterium Flavobacterium, Alcaligenes, Pseudomonas, Bacillus* or *Cyanobacterium* such as—for example—*Synechocystis* and other bacteria described in Brock Biology of Microorganisms Eighth Edition (pages A-8, A-9, A10 and A11). In some embodiments, the cells or non-human, organisms comprising a recombinant gene described herein is a plant cell or plant (as defined herein). In some embodiments, the plant is hemizygous for the recombinant gene. In some embodiments, the plant is homozygous for the recombinant gene.

other example of microorganisms are those capable to infect plants and to transfer DNA into their genome, especially bacteria of the genus *Agrobacterium*, like *Agrobacterium tumofaciens* and *rhizogenes*. Examples of yeasts are *Candida, Saccharomyces, Hansenula* and *Pichia*. Examples of fungi are *Aspergillus, Trichoderma, Ashbya, Neurospara, Fusarium*, and *Beauveria*.

In some embodiments, the host cell is a plant cell, a plant, a plant seed or other plant part, a non-human animal or a multicellular microorganism. The term "plant" as used herein refers to a photosynthetic, eukaryotic multicellular organism. Plants encompass green algae (Chlorophyta), red algae (Rhodophyta), Glaucophyta, mosses and liverworts (bryophytes), seedless vascular plants (horsetails, club mosses, ferns) and seed plants (angiosperms and gymnosperms). The term "plant" encompasses whole plants, ancestors and progeny of the plants and plant parts, including seeds, shoots, stems, leaves, roots, flowers, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen, microspores and propagules, again wherein each of the aforementioned comprises the gene/nucleic acid of interest.

The term "plant parts" as used herein encompasses all components of a plant including seeds, shoots, stems, leaves, roots, flowers, and plant tissues and plant organs, plant cells, suspension cultures, callus tissue, embryos, meristematic regions, gametophytes, sporophytes, pollen, microspores and propagules. A "Propagule" is any kind of organ, tissue, or cell of a plant capable of developing into a complete plant. A propagule can be based on vegetative reproduction (also known as vegetative propagation, vegetative multiplication, or vegetative cloning) or sexual reproduction. A propagule can therefore be seeds or parts of the non-reproductive organs, like stem or leave. In particular, with respect to Poaceae, suitable propagules can also be sections of the stem, i.e., stem cuttings.

A plant, plant part or seed comprising a recombinant gene or a vector described herein is specifically contemplated. The recombinant gene or vector may be present in the cytoplasm of the organism or may be incorporated into the genome either heterologous or by homologous recombination. Host cells, in particular those obtained from plants or animals, may be introduced into a developing embryo in order to obtain mosaic or chimeric organisms, i.e. organisms, i.e. plants, comprising the host cells of described herein. Suitable organisms are, for example, all organisms which are suitable for the expression of recombinant genes.

Plants expressing genes, which encode enzymes that affect the integrity of the insect cuticle form yet another aspect of the invention. Such genes include those encoding, e.g., chitinase, proteases, lipases and also genes for the production of nikkomycin, a compound that inhibits chitin synthesis, the introduction of any of which is contemplated to produce insect resistant maize plants. Genes that code for activities that affect insect molting, such those affecting the production of ecdysteroid UDP-glucosyl transferase, also fall within the scope of the useful transgenes of the present invention.

Genes that code for enzymes that facilitate the production of compounds that reduce the nutritional quality of the host plant to insect pests are also encompassed by the present invention. It may be possible, for instance, to confer insecticidal activity on a plant by altering its sterol composition. Sterols are obtained by inserts from their diet and are used for hormone synthesis and membrane stability. Therefore alterations in plant sterol composition by expression of novel genes, e.g., those that directly promote the production of undesirable sterols or those that convert desirable sterols into undesirable forms, could have a negative effect on insect growth and/or development and hence endow the plant with insecticidal activity. Lipoxygenases are naturally occurring plant enzymes that have been shown to exhibit anti-nutritional effects on insects and to reduce the nutritional quality of their diet. Therefore, further embodiments of the invention concern plants with enhanced lipoxygenase activity which may be resistant to insect feeding.

The nature of the plants, plant parts and seeds are not limited; for example, the plant, plant part or seed can be monocotyledonous or dicotyledonous. In some embodiments, the plant, plant part or seed is from a monocotyledonous plant. In some embodiments, the plant or plant part is from a dicotyledonous plant. Examples of plant cells finding use according to the disclosure include, but are not limited to, cells (or entire plants or plant parts) derived from the genera: *Ananas, Musa, Vitis, Fragaria, Lotus, Medicago, Onobtychis, Trifolium, Trigonella, Vigna, Citrus, Carica, Persea, Prunus, Syragrus, Theobroma, Coffee, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Mangifera, Cichorium, Helianthus, Lactuca, Bromus, Asparagus, Antirrhinum, Heterocallis, Nemesia, Pelargonium, Panicum, Pennisetum, Ranunculus, Senecio, Salpiglossis, Cucurbita, Cucumis, Browaalia, Lolium, Malus, Apium, Gossypiumk, Vicia, Lathyrus, Lupinus, Pachyrhizus, Wisteria, Stizolobium, Agrostis, Phleum, Dactylis, Sorghum, Setaria, Zea, Oryza, Triticum, Secale, Avena, Hordeum, Saccharum, Poe, Festuca, Stenotaphrum, Cynodon, Coix, Olyreae, Phareae, Glycine, Pisum, Psidium, Passiflora, Cicer, Phaseolus, Lens*, and *Arachis*.

In some embodiments the plant Cells include cells (or entire plants or plant parts) from the family of poeceae, such as the genera *Hordeum, Secale, Avena, Sorghum, Andropogon, Holcus, Panicarn, Oryza, Zea, Triticum*, for example the genera and species *Hordeum vulgare, Hordeum jubatum, Hordeum murinum, Hordeum secalinum, Hordeum distichon, Hordeum aegiceras, Hordeum hexastichon, Hordeum hexastichum, Hordeum irregulare, Hordeum sativum, Hordeum secalinum, Secale cereale, Avena sativa, Avena fatua, Avena byzantine, Avena fatua* var. *saliva, Avena hybrida, Sorghum bicolor, Sorghum halepense, Sorghum saccharatum, Sorghum vulgare, Andropogon drummondii, Holcus bicolor, Holcus sorghum, Sorghum aethinpicum, Sorghum arundinaceum, Sorghum caffrorum, Sorghum cernuum, Sorghum dochna, Sorghum drummondii, Sorghum durra, Sorghum guineense, Sorghum lancoolatum, Sorghum nervosum, Sorghum saccharatum, Sorghum subglabrescens, Sorghum verticilliflorum, Sorghum vulgare, Holcus halepensis, Sorghum miliaceum, Panicum militaceum, Oryza saliva, Oryza latifolia, Zea mays, Triticum aestivum, Triticum durum, Triticum turgidum, Triticum hybernum, Triticum macho, Triticum sativum* or *Triticum vulgare*.

In some embodiments, plants to be used are oil fruit crops which comprise large amounts of lipid compounds, such as peanut, oilseed rape, canola, sunflower, safflower, poppy, mustard, hemp, castor-oil plant, olive, sesame, Calendula, Punica, evening primrose, mullein, thistle, wild roses, hazelnut, almond, macadamia, avocado, bay, pumpkin/squash, linseed, soybean, pistachios, borage, trees (oil palm, coconut, walnut) or crops such as maize, wheat, rye, oats, triticale, rice, barley, cotton, cassava, pepper, *Tagetes*, Solanaceae plants such as potato, tobacco, eggplant and tomato, *Vicia* species, pea, alfalfa or bushy plants (coffee, cacao, tea), *Salix* species, and perennial grasses and fodder crops. Plants according to the invention may be oil crop plants such as peanut, oilseed rape, canola, sunflower, safflower, poppy, mustard, hemp, castor-oil plant, olive, Calendula, Punica, evening primrose, pumpkin/squash, linseed, soybean, borage, trees (oil palm, coconut).

Methods for producing plants or plant parts, including plant tissue, plant organ, plant or seed comprising introducing a recombinant gene of vector described herein into a plant cell and regenerating the plant cell to form a plant tissue, plant organ, plant or seed are also contemplated.

Methods of providing pesticidal activity to a plant comprising introducing a recombinant gene of vector described herein comprising a nucleotide sequences that encodes a pesticidal protein into a plant cell and regenerating the plant cell to form a plant or plant part, including plant tissue, plant organ, plant or seed, thereby providing pesticidal activity to the plant, are also contemplated. In some embodiments, the pesticidal activity is insecticidal activity.

Recombinant genes can be introduced into plant cells in a number of art-recognized ways. Plant species may be transformed with the DNA construct or recombinant gene described herein by the DNA-mediated transformation of plant cell protoplasts and subsequent regeneration of the plant from the transformed protoplasts in accordance with procedures well known in the art.

Any plant tissue capable of subsequent clonal propagation, whether by organogenesis or embryogenesis, may be transformed with a vector described herein. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristems, axillary buds; and root meristems), and induced meristem tissue (e.g., cotyledon meristem and ultilane meristem).

Plants may take a variety of forms. For example, the plants may be chimeras of transformed cells and non-transformed cells; the plants may be clonal transformants (e.g., all cells transformed to contain the recombinant gene); the plants may comprise grafts of transformed and untransformed tissues (e.g., a transformed root stock grafted to an untransformed scion in citrus species). The transformed plants may be propagated by a variety of means, such as by clonal propagation or classical breeding techniques. For example, first generation (or T1) transformed plants may be selfed to give homozygous second generation (or T2) transformed plants, and the T2 plants further propagated through classical breeding techniques. A dominant selectable marker (such as npt II) can be associated with the recombinant gene to assist in breeding.

Transformation of plants can be undertaken with a single DNA molecule or multiple DNA molecules (i.e., co-transformation), and both these techniques are suitable for use with the recombinant genes described herein. Numerous transformation vectors are available for plant transformation, and the recombinant genes of this invention can be used in conjunction with any such vectors. The selection of vector will depend upon the chosen transformation technique and the target species for transformation.

A variety of techniques are available and known to those skilled in the art for introduction of constructs into a plant cell host. Exemplary techniques include transformation with DNA employing *A. tumefaciens* or *A. rhizogenes* as the transforming agent, liposomes, PEG precipitation, electroporation, DNA injection, direct DNA uptake, microprojectile bombardment, particle acceleration, and the like (See, for example, EP 295959 and EP 138341) (see below). However, cells other than plant cells may be transformed with the recombinant genes described herein. The general descriptions of plant expression vectors and reporter genes, and *Agrobacterium* and *Agrobacterium*-mediated gene transfer, can be found in Gruber et al. (1993).

Expression vectors containing genomic or synthetic fragments can be introduced into protoplasts or into intact tissues or isolated cells. Expression vectors may be introduced into intact tissue. General methods of culturing plant tissues are provided for example by Maki et al., (1993); and by Phillips et al, (1988). Expression vectors may be introduced into maize or other plant tissues using a direct gene transfer method such as microprojectile-mediated delivery, DNA injection, electroporation and the like. Expression vectors may also be introduced into plant tissues using the microprojectile media delivery with the biolistic device. See, for example, Tomes et al. (1995). The vectors of the invention can not only be used for expression of structural genes but may also be used in exon-trap cloning, or promoter trap procedures to detect differential gene expression in varieties of tissues (Lindsey 1993; Auch & Reth 1990).

In some embodiments, the binary type vectors of Ti and Ri plasmids of *Agrobacterium* app. Ti-derived vectors are used to transform a wide variety of higher plants, including monocotyledonous and dicotyledonous plants, such as soybean, cotton, rape, tobacco, and rice (Pacciotti 1985: Byrne 1987; Sukhapinda 1987; Lorz 1985; Potrykus, 1985; Park 1985: Hiei 1994). The use of T-DNA to transform plant cells has received extensive study and is amply described (EP 120516; Hoekema, 1985; Knauf, 1983; and An 1985).

Other transformation, methods are available to those skilled in the art, such as direct uptake of foreign DNA constructs (see EP 295959), techniques of electroporation (Fromm 1986) or high velocity ballistic bombardment with metal particles coated with the nucleic acid constructs (Kline 1987, and U.S. Pat. No. 4,945,050). Once transformed, the cells can be regenerated by those skilled in the art. Of particular relevance are the recently described methods to transform foreign genes into commercially important crops, such as rapeseed (De Block 1989), sunflower (Everett 1987), soybean (McCabe 1988; Hinchee 1988; Chee 1989; Christou 1989; EP 301749), rice (Hiei 1994), and corn (Gordon-Kamm 1990; Fromm 1990).

Those skilled in the art will appreciate that the choice of method might depend on the type of plant, i.e., monocotyledonous or dicotyledonous, targeted for transformation. Suitable methods of transforming plant cells include, but are not limited to, microinjection (Crossway 1986), electroporation (Riggs 1986), *Agrobacterium*-mediated transformation (Hinchee 1988), direct gene transfer (Paszkowski 1984), and ballistic particle acceleration using devices available from Agracetus, Inc., Madison, Wis. And BioRad, Hercules, Calif. (see; for example, U.S. Pat. No. 4,945,050; and McCabe 1988). Also see, Weissinger 1988; Sanford 1987 (onion); Christou 1988 (soybean); McCabe 1988 (soybean); Datta 1990 (rice); Klein 1988 (maize); Klein 1988 (maize); Klein 1988 (maize); Fromm 1990 (maize); and Gordon Kamm 1990 (maize); Svab 1990 (tobacco chloroplast); Koziel 1993 (maize); Shimamoto 1989 (rice); Christou 1991 (rice); European Patent Application EP 0 332 581 (orchardgrass and other Pooideae); Vasil 1993 (wheat); Weeks 1993 (wheat).

Methods using either a form of direct gene transfer or *Agrobacterium*-mediated transfer usually, but not necessarily, are undertaken with a selectable marker, which may provide resistance to an antibiotic (e.g., kanamycin, hygromycin or methotrexate) or a herbicide (e.g., phosphinothricin). For certain plant species, different antibiotic or herbicide selection markers may be preferred. Selection markers used routinely in transformation include the nptII gene which confers resistance to kanamycin and related antibiotics (Messing & Vierra, 1982; Bevan 1983), the bar gene which confers resistance to the herbicide phosphinothricin (White 1990, Spencer 19901, the hph gene which confers resistance to the antibiotic hygromycin (Blochlinger & Diggelmann), and the dhfr gene, which confers resistance to methotrexate (Bourouis 1983).

Methods for the production and further characterization of stably transformed plants are well-known to the person skilled in the art. As an example, transformed plant cells are placed in an appropriate selective medium for selection of transformed cells, which are then grown to callus. Shoots are grown from callus. Plantlets are generated from the shoot by growing in rooting, medium. The various constructs normally will, be joined to a marker for selection in plant cells. Conveniently, the marker may be resistance to a biocide (particularly an antibiotic, such as kanamycin, G418, bleomycin, hygromycin, chloramphenicol, herbicide, or the like). The particular marker used will allow for selection of transformed cells as compared to cells lacking the DNA, which has been introduced. Components of DNA constructs including transcription cassettes of this invention may be prepared from sequences, which are native (endogenous) or foreign (exogenous) to the host. By "foreign" it is meant that the sequence is not found in the wild-type host into which the construct is introduced. Heterologous constructs will contain at least one region, which is not native to the gene from which the transcription-initiation-region is derived.

To confirm the presence of the transferred polynucleotide of interest in transformed cells and plants, a variety of assays may be performed. Such assays include, for example. "molecular biological" assays well known to those of skill in the art, such as Southern and Northern blotting, in situ hybridization and nucleic acid-based amplification methods such as PCR or RT-PCR or TaqMan; "biochemical" assays, such as detecting the presence of a protein product, e.g., by immunological means (ELISAs and Western blots) or by enzymatic function; plant part assays, such as seed assays; and also, by analyzing the phenotype of the whole regenerated plant, e.g., for disease or pest resistance.

DNA may be isolated from cell lines or any plant parts to determine the presence of the preselected nucleic acid segment through the use of techniques well known to, those skilled in the art, Note that intact sequences will not always be present, presumably due to rearrangement or deletion of sequences in the cell.

In some embodiments, the presence of nucleic acid elements introduced through the methods of this invention may be determined by polymerase chain reaction (FOR). Using these technique discreet fragments of nucleic acid are amplified and detected by gel electrophoresis. This type of analysis permits one to determine whether a preselected nucleic acid segment is present in a stable transformant, but does not prove integration of the introduced preselected nucleic acid segment into the host cell genome, in addition, it is not possible using PCR techniques to determine whether transformants have exogenous genes introduced into different sites in the, genome, i.e., whether transformants are of independent origin. It is contemplated that using FOR techniques it would be possible to clone fragments of the host genomic DNA adjacent to an introduced preselected DNA segment.

Known methods of FOR include, but are not limited to, methods using paired primers, nested primers, single specific primers, degenerate primers, gene specific primers, vector-specific primers, partially mismatched primers, and the like.

Positive proof of DNA integration into the host genome and the independent identities of transformants may be determined using the technique of Southern hybridization. Using this technique specific DNA sequences that were introduced into the host genome and flanking host DNA sequences can be identified, Hence the Southern hybridization pattern of d given transformant serves as an identifying characteristic of that transformant. In addition it is possible through Southern hybridization to demonstrate the presence of introduced preselected DNA segments in high molecular weight DNA, i.e., confirm that the introduced preselected, DNA segment has been integrated into the host cell genome. The technique of Southern hybridization provides information that is obtained using FOR, e.g., the presence of a preselected DNA segment, but also demonstrates integration into the genome and characterizes each individual transformant.

It is contemplated that using the techniques of dot or slot blot hybridization which are modifications of Southern hybridization techniques one could obtain the same information that is derived from FOR, e.g., the presence of a preselected DNA segment.

Both FOR and Southern hybridization techniques can be used to demonstrate transmission of a preselected DNA segment to progeny. In most instances the characteristic Southern hybridization pattern for a given transformant will segregate in progeny as one or more Mendelian genes (Spencer 1992); Laursen 1994) indicating stable inheritance of the gene. The non-chimeric nature of the callus and the parental transformants (RU) was suggested by germline transmission and the identical Southern blot hybridization patterns and intensities of the transforming DNA in callus, RU plants and R1 progeny that segregated for the transformed gene.

Whereas DNA analysis techniques may be conducted using DNA isolated from any part of a plant, RNA may only be expressed in particular cells or tissue types and hence it will be necessary to prepare RNA for analysis from these tissues. PCR techniques may also be used for detection and quantitation of RNA produced from introduced preselected DNA segments. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and will only demonstrate the presence or absence of an RNA species.

While Southern blotting and PCR may be used to detect the preselected DNA segment in question, they do not provide information as to whether the preselected DNA segment is being expressed. Expression may be evaluated by specifically identifying the protein products of the introduced preselected DNA segments or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures, of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures may also be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed.

Very frequently the expression of a gene product is determined by evaluating the phenotypic results of its expression. These assays, also may take many forms including but not limited to analyzing changes in the chemical composition, morphology, or physiological properties of the plant. Morphological changes may include greater stature or thicker stalks. Most often changes in response of plants or plant parts to imposed treatments are evaluated under carefully controlled conditions termed bioassays.

Use of the nucleic acid having constitutive promoter activity described herein is provided to regulate expression of an operably linked nucleic acid in a plant or to identify other nucleic acid having constitutive promoter activity.

A method of producing food, feed, or an industrial product includes a) obtaining the plant, plant part or seed, of the invention, and b) preparing the food, feed or industrial product from the plant, plant part or seed. The method may also include where a) the food or feed is oil, meal, grain, starch, flour or protein, or b) the industrial product is biofuel, fiber, industrial chemicals, a pharmaceutical or a nutraceutical.

It is to be understood that this invention is not limited to the particular methodology, proto-cols, cell lines, plant species or genera, constructs, and reagents described as such. It is also to be understood that the terminology used herein is for the purpose of describing particular embodiments only and is not intended to limit the scope of the present invention, which will be limited only by the appended claims. It must be noted that as used herein and in the appended claims, the singular forms "a," "and," and "the" include plural reference unless the context clearly dictates otherwise. Thus, for example, reference to "a vector" is a reference to one or more vectors and includes equivalents thereof known to those skilled in the art, and so forth.

SEQUENCE LISTING

This application contains, as a separate part of the disclosure, a Sequence Listing in computer readable form (Filename: 202017P2_Seqlisting.txt; Size: 5,022 bytes; Created: Nov. 20, 2020), which is incorporated by reference in its entirety.

EXAMPLES

Unless stated otherwise in the Examples, all recombinant DNA techniques are carried out according to standard protocols as described in Sambrook and Russell (2001) Molecular Cloning: A Laboratory Manual, Third Edition, Cold Spring Harbor Laboratory Press, NY, in Volumes 1 and 2 of Ausubel et al. (1994) Current Protocols in Molecular Biology, Current Protocols USA and in Volumes I and II of Brown (1998) Molecular Biology LabFax, Second Edition, Academic Press (UK). Standard materials and methods for plant molecular work are described in Plant Molecular Biology Labfax (1993) by R. D. D. Croy, jointly published by BIOS Scientific Publications Ltd (UK) and Blackwell Scientific Publications, UK. Standard materials and methods for polymerase chain reactions can be found in Dieffenbach and Dveksler (1995) PCR Primer A Laboratory Manual, Cold Spring Harbor Laboratory Press, and in McPherson at al. (2000) PCR—Basics: From Background to Bench, First Edition, Springer Verlag, Germany.

Example 1—Cloning of the Promoter Region of Soybean Gene Glyma13g33190

To clone the promoter region of soybean gene glyma13g33190 (Soybase annotation Glyma 1.1), designated P-bdc16-1.2, SEQ ID NO: 1, a plasmid that contains the promoter sequence of glyma13g33190 gene from Thorne was used as a template for PCR amplification of SEQ ID NO: 1 using a Q5 High-Fidelity DNA Polymerases kit from NEB (Ipswich, MA USA). PCR was performed on the plasmid DNA with adapter and sequence-specific primers (Forward primer: ctccgaatatctottagttgaaaaaaaacatttc (SEQ ID NO: 5); Reverse primer: TTTCTTTCTTGCTTTCTTAT-GATTCTCTTCTTCTC (SEQ ID NO: 6)). The adaptor is a short DNA sequence that is complementary to the destination vector sequence adjacent to the cloning site. PCR products were resolved using electrophoresis on a 0.8% (w/v) agarose gel. Fragments with the size of around 1080 bp were excised from the gel, purified and assembled into our proprietary plant gene expression vector pBay01339, which was pre-digested with SbfI and BsgI enzymes, with the Gibson assembly kit according to manufacturer's instructions (SGI-DNA, Madison, Wis., USA). The resulting vector pBay02059 was sequenced and aligned with the P-bdc16-1.2 sequence from Thorne and a 100% alignment was found.

P-bdc16-1.2 was originally cloned from soybean (*Glycine Max* cultivar Thorne) genomic DNA with PCR amplification.

Example 2—Promoter Deletion Variants

Figure 2:
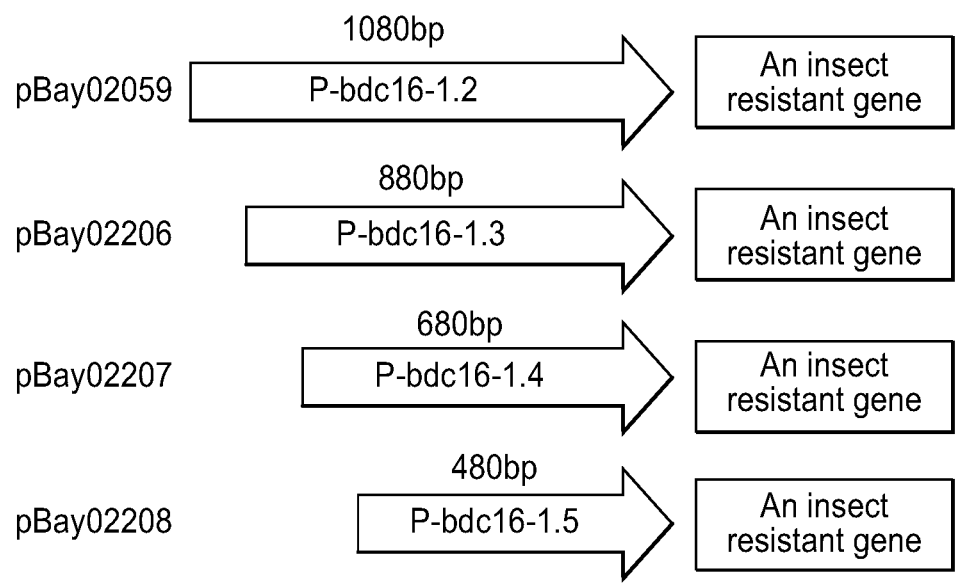
FIG. 2 provides schematics of various deletion variants of SEQ ID NO: 1 (P-bdc16-1.2) set forth in SEQ ID NO: 2 (P-bdc16-1.3), SEQ ID NO: 3 (P-bdc16-1.4) and SEQ ID NO: 4 (P-bdc16-1.5), respectively, as described in Example 2.

A series of 200 bp deletions from the 5' end of P-bdc16-1.2 were made via PCR-mediated cloning. Briefly, the promoter regions of soybean gene glyma13g33190 with the size of 480 bp (SEQ ID NO: 4), 680 bp (SEQ ID NO: 3), and 880 bp (SEQ ID NO: 2) were PCR amplified from plasmid DNA of pBay02059. PCR was done in the same way as described in Example 1. PCR primers consist of adaptor and sequence-specific primer to each of these truncated promoters, which share the same 3' end. The adaptor is a short DNA sequence that is complementary to the destination vector sequence adjacent to the cloning site. In this case, the destination vector is pBay02059. PCR products were resolved using electrophoresis on a 1% (w/v) agarose gel. Fragments with the size of 480 bp (SEQ ID NO: 4), 680 bp (SEQ ID NO: 3), and 880 bp (SEQ ID NO: 2) were excised from the gel, purified and assembled into pBay02059, pre-digested with SbfI and BsgI enzymes, with the Gibson assembly kit according to manufacturer's instructions (SGI-DNA, Madison, Wis., USA). The resulting plasmids pBay2206, pBay02207, pBay02208 contain P-bdc16-1.3 (880 bp SEQ ID NO: 2), P-bdc16-1.4 (680 bp SEQ ID NO: 3), P-bdc16-1.5 (480 bp SEQ ID NO: 4), respectively. The results are shown in FIG. 2.

Example 3—Tobacco Transient Assay

Figure 3:
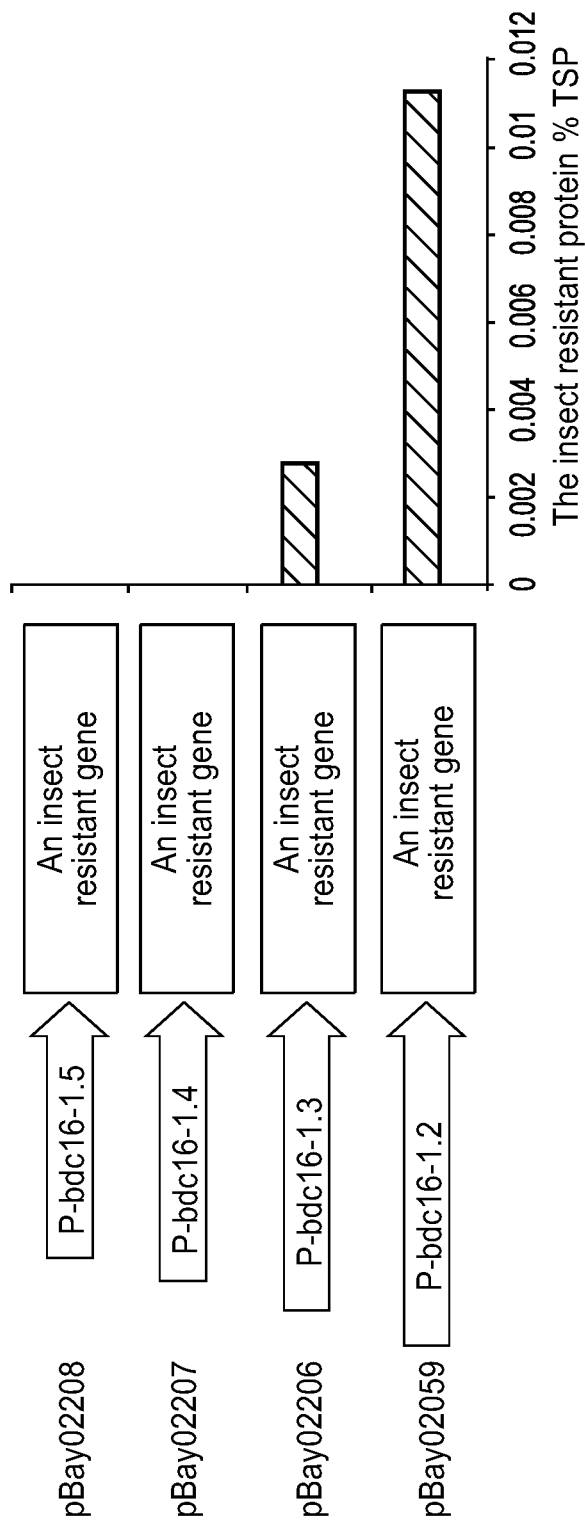
FIG. 3 provides a graph showing the level of expression of the insect resistant gene when operably linked to the nucleotide sequences set forth in SEQ ID NOs 1, 2, 3, and 4.

Plasmid DNA of pBay0.2059, pBay2206, pBay02207, and pBay02208 were transformed into *Agrobacterium* strain EHA105 (Hood et al., 1986). The resulting agrobacteria containing these plasmids were used to agroinfiltrate fully expanded young leaves of *Nicotiana benthamiana* (Wydro et al., 2006). Infiltrated leaf samples were collected two days after agroinfiltration. The reporter (an insect resistant gene) expression (percentage of total soluble proteins, % TSP) was analyzed in these samples. The results are shown in FIG. 3.

Example 4—Additional Expression Analysis

Figure 4:
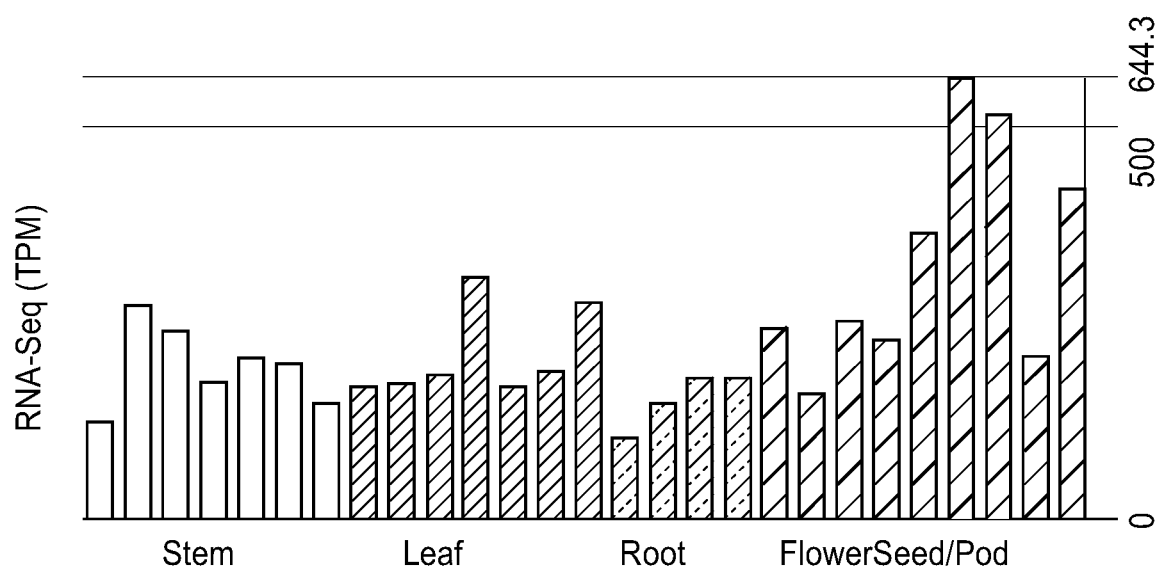
FIG. 4 is a graph showing expression data (RNA-seq) for the native soybean glyma13g33190 from which the promoter P-bdc16-1.2 (SEQ ID NO: 1) is derived.

Expression data (RNA-seq) for the native soybean glyma13g33190 from which the promoter P-bdc16-1.2 (SEQ ID NO: 1) is derived was performed. RNA-seq data were generated at GENEWIZ (South Plainfield, NJ) with soybean tissues (cultivar Thorne), As shown in FIG. 4, P-bdc16-1.2 (SEQ ID NO: 1) is constitutively expressed in all plant tissues tested, including stem, leaf, root and flower seed/pod.

Example 5—Stable Transformation in Soybean Cultivars

Figure 5:
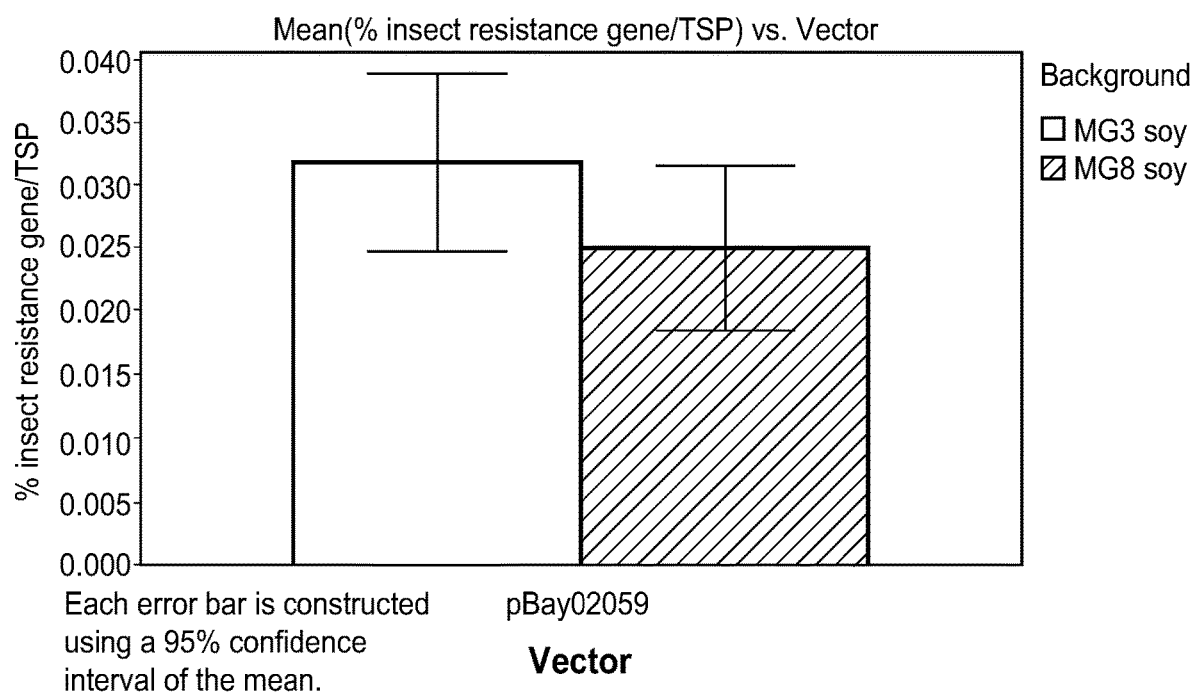
FIG. 5 is a bar graph showing the percent insect resistant gene expressed per total soluble protein (TSP) in primary transformants (TO) of two soybean cultivars (maturity group (MG3) and maturity group 8 (MG8)).

Stable transformation events were created using an *A. tumefaciens* transformation method that utilized starting material from mature half seeds as described in *Agrobacterium* Protocols pp 275-284 (Loth et al., 2015). Plasmid DNA from vector pBay02059 was transformed into *Agrobacterium* strain EHA105 (Hood et al 1986) was also, used for stable transformation experiments. Starting material was sourced from two soybean cultivars amenable to transformation that represented two distinct maturity groups (MG), MG3 and MG8. Successful gene transfer was confirmed by both herbicide selection and copy number PCR to select T0 events containing a single T-DNA insertion. See Table 1 and FIG. 5.

TABLE 1

| Level | Number | Mean | Std. Error | Lower 95% | Upper 95% |
|---|---|---|---|---|---|
| MG3 soy | 24 | 0.031533 | 0.00335 | 0.02480 | 0.03826 |
| MG8 soy | 27 | 0.024887 | 0.00316 | 0.01854 | 0.03123 |

Figure 6:
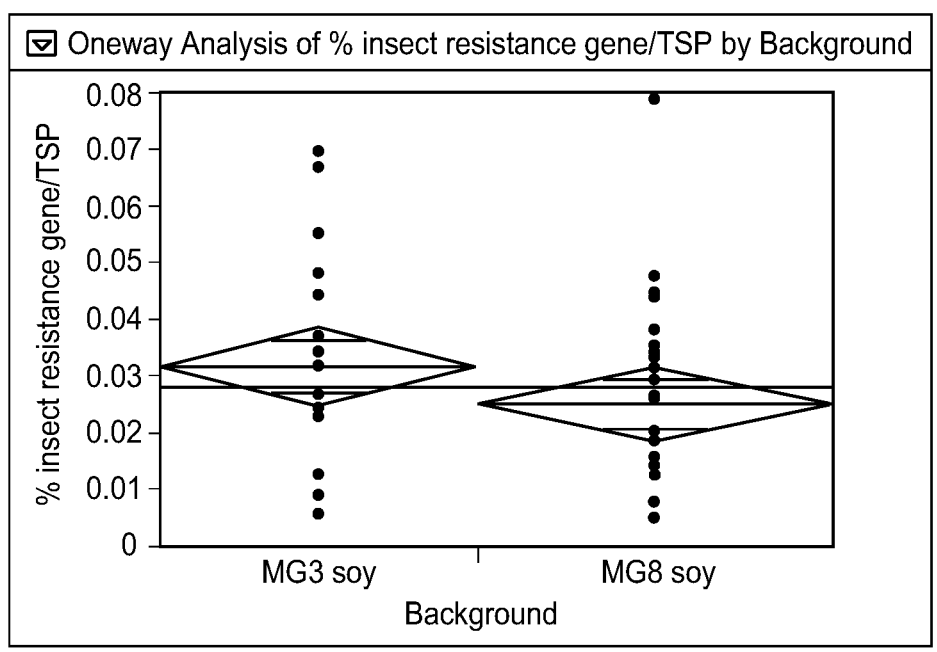
FIG. 6 is a scatter plot showing the percent insect resistant gene expressed per total soluble protein (TSP) expressed in primary transformants (TO) of two soybean cultivars (MG3 and MG8)

After positive event identification, samples were taken at the v2-v3 growth stage to confirm relative protein expression by ELISA (FIG. 6) utilizing an assay specific to the introduced insect resistance gene.

Example 6—Expression of Polynucleotides of Interest in Soybean Cultivars

Figure 7:
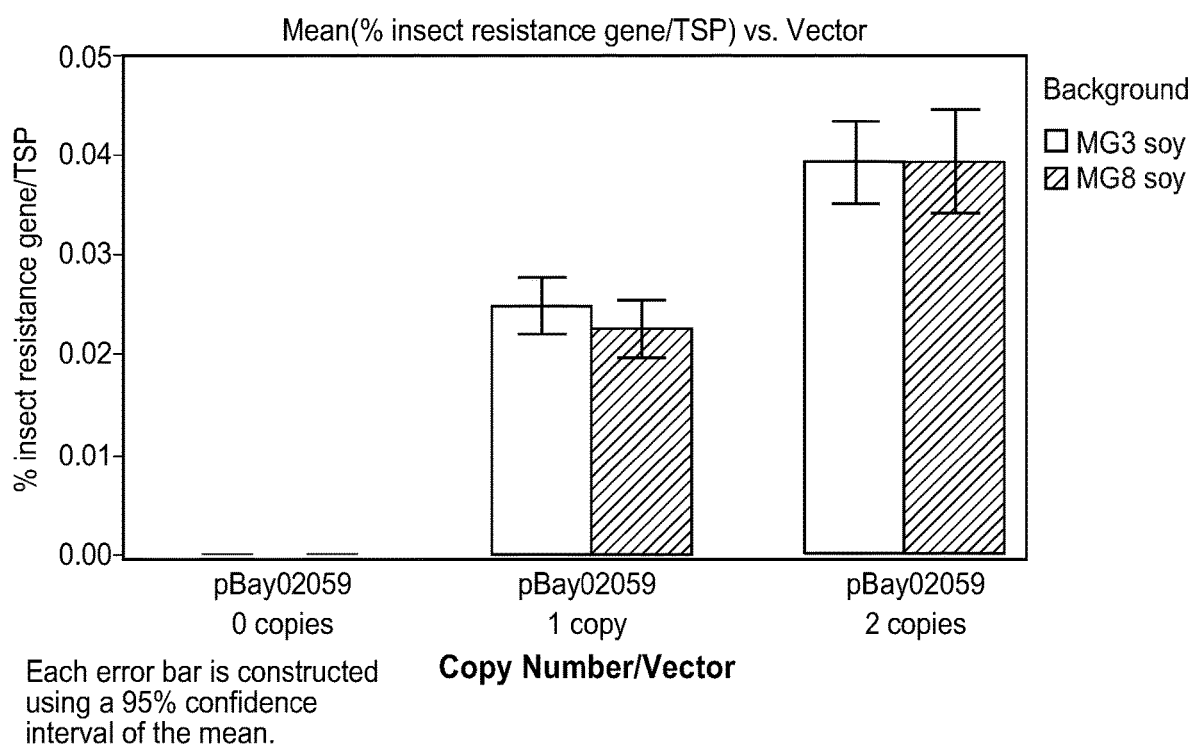
FIG. 7 is a bar graph showing the percent insect resistant gene expressed per total soluble protein (TSP) as one or two copies of the T1 segregating events from pBay02059 vector in two soybean cultivars (M03 and MG8).
Figure 8:
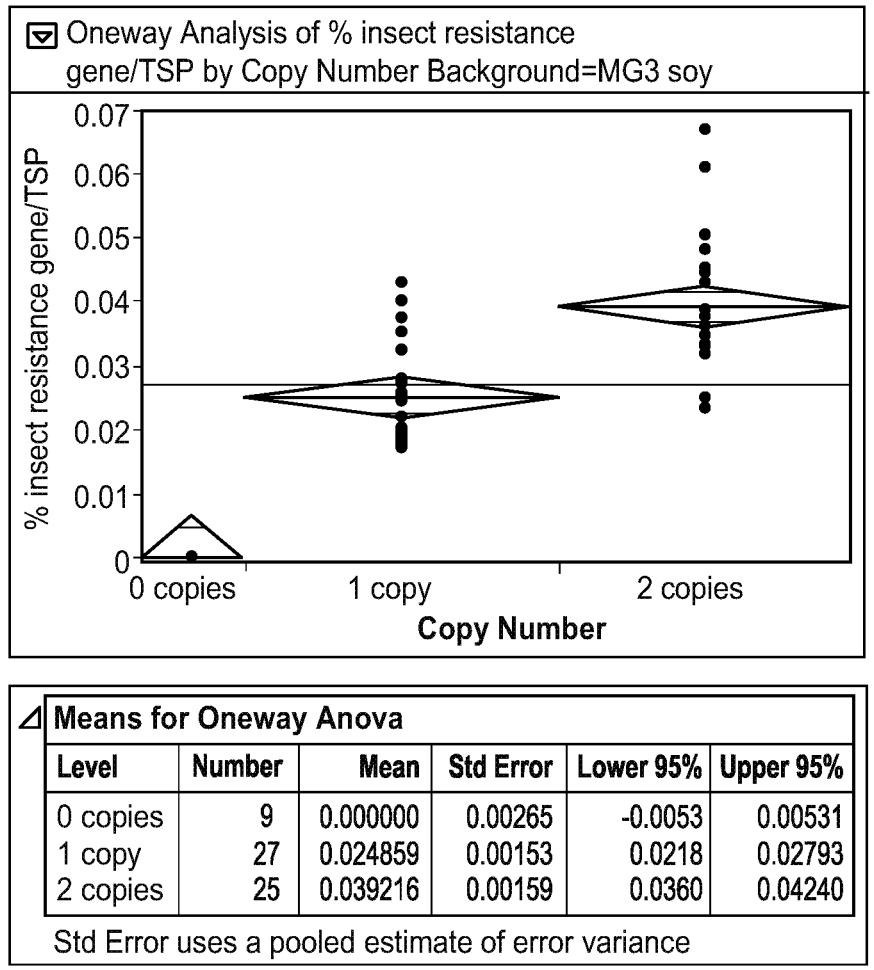
FIG. 8 is a scatter plot showing the percent insect resistant gene expressed per total soluble protein (TSP) as one or two copies of the T1 segregating events from pBay02059 vector in the MG3 soybean cultivar.

Events were selected representing the TO generation interquartile range of protein expression for the insect resistance gene (MG3 soy n=9 events, MG8 soy n=8 events). Segregating T1 seed was sown and plants were grown under typical greenhouse conditions. Shortly after emergence all plants were sampled for copy number and analyzed for both the insect resistance gene and the herbicide selectable marker. See Table 2 and FIGS. 7 and 8.

TABLE 2

| Level | Number | Mean | Std. Error | Lower 95% | Upper 95% |
|---|---|---|---|---|---|
| MG3 Soy | | | | | |
| 0 copies | 9 | 0.000000 | 0.00265 | −0.0053 | 0.00531 |
| 1 copy | 27 | 0.024859 | 0.00153 | 0.0218 | 0.02793 |
| 2 copies | 25 | 0.039216 | 0.00159 | 0.0360 | 0.04240 |
| MG8 Soy | | | | | |
| 0 copies | 8 | 0.000000 | 0.00327 | −0.0066 | 0.00657 |
| 1 copy | 23 | 0.022622 | 0.00193 | 0.0187 | 0.02650 |
| 2 copies | 24 | 0.039346 | 0.00189 | 0.0356 | 0.04314 |

Figure 9:
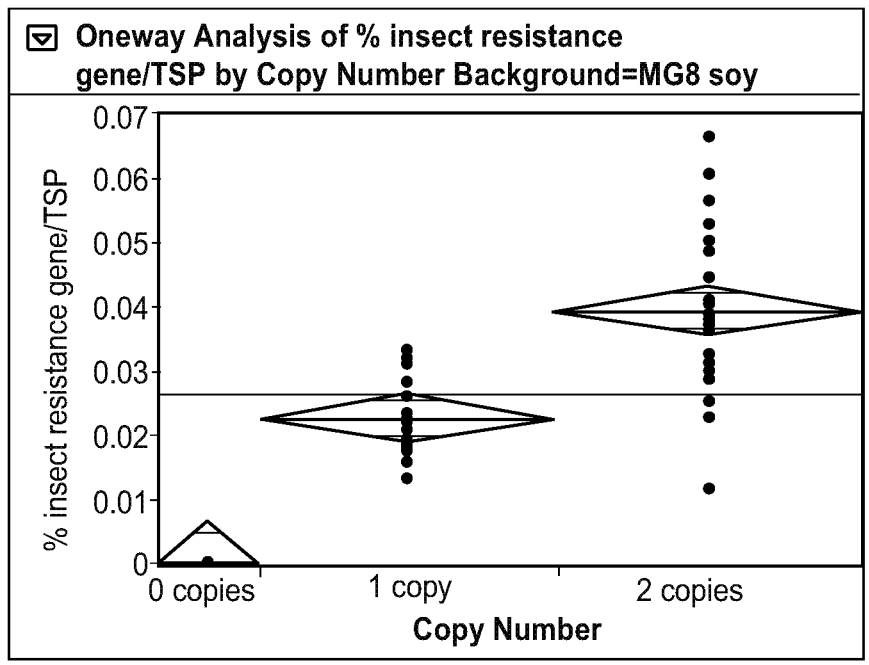
FIG. 9 is a scatter plot showing the percent insect resistant gene expressed per total soluble protein (TSP) expressed as one or two copies of the T1 segregating events from pBay02059 vector in the MG8 cultivar.

ELISA analysis samples were taken at the v3-v4 growth stage from each event as follows—one 0 copy (null) and up to three for both 1 copy (hemizygous) and 2 copies (homozygous) of the vector. See FIG. 9.

REFERENCES

Hood, E. E G. L. Helmer, R. T. Fraley, and M.-D. Chilton. 1986. The hypervirulence of *Agrobacterium tumefaciens* A281 is encoded in a region of pTiBo542 outside of T-DNA. J. Bacterial. 168:1291-1301.

Wydro M., E. Kozubek, and P. Lehmann. 2006. Optimization of transient *Agrobacterium*-mediated gene expression system in leaves of *Nicotiana benthamiana*. Acta Biochimica Poionica. Vol 53, No 2/2006, 289-298.

What is claimed is:

1. A recombinant gene for regulating expression of a polynucleotide of interest, said recombinant gene comprising a heterologous nucleic acid having constitutive promoter activity comprising the nucleotide sequence of SEQ ID NO: 1 or SEQ ID NO: 2.

2. The recombinant gene of claim 1, wherein said recombinant gene further comprises at least one polynucleotide of interest being operatively linked to the nucleic acid having constitutive promoter activity.

3. The recombinant gene of claim 1, wherein the polynucleotide of interest encodes an insecticidal protein or a herbicide selectable marker.

4. A vector comprising the recombinant gene according to claim 1.

5. The vector of claim 4, wherein said vector is an expression vector.

6. A host cell comprising a heterologous nucleic acid having constitutive promoter activity
comprising the nucleotide sequence of SEQ ID NO: 1 or SEQ ID NO: 2.

7. The host cell of claim 6, wherein said host cell is a plant cell.

8. A plant, plant part or seed comprising a heterologous nucleic acid having constitutive promoter activity
comprising the nucleotide sequence of SEQ ID NO: 1 or SEQ ID NO: 2.

9. A method for expressing a polynucleotide of interest in a host cell comprising
   (a) introducing the recombinant gene according to claim 1 into said host cell, and
   (b) expressing at least one polynucleotide of interest in said host cell.

10. The method of claim 9, wherein said host cell is a plant cell.

11. The method of claim 9, wherein the polynucleotide of interest encodes a protein that accumulates to a detectable amount of about 0.01%-1.15% of the extracted total soluble proteins.

12. A method for producing a plant or plant part comprising
   (a) introducing the recombinant gene according to claim 1 into a plant cell; and
   (b) regenerating said plant cell to form a plant or plant part.

13. A method of providing pesticidal activity in a plant comprising
   (a) introducing the recombinant gene according to claim 1 into a host cell, and
   (b) expressing a polynucleotide that encodes a pesticidal protein in said host cell, thereby providing pesticidal activity in the plant.

14. The method of claim 13, wherein the pesticidal protein is an insecticidal protein.

15. A method of producing food, feed, or an industrial product comprising
   a) obtaining the plant, plant part or seed, of claim 8; and
   b) preparing the food, feed or industrial product from the plant, plant part or seed.

16. The method of claim 15 wherein
   a) the food or feed is oil, meal, grain, starch, flour or protein; or
   b) the industrial product is biofuel, fiber, industrial chemicals, a pharmaceutical or a nutraceutical.

* * * * *